| (12) | United States Patent | (10) Patent No.: | US 9,050,481 B2 |
|---|---|---|---|
| | Fenton et al. | (45) Date of Patent: | Jun. 9, 2015 |

(54) DECONTAMINATION

(75) Inventors: Marcus Brian Mayhall Fenton, Cambridgeshire (GB); James Oliver French, Cambridgeshire (GB)

(73) Assignee: Tyco Fire & Security GmbH, Neuhausen am Rheinfall (DE)

( * ) Notice: Subject to any disclaimer, the term of this patent is extended or adjusted under 35 U.S.C. 154(b) by 897 days.

(21) Appl. No.: 12/741,941

(22) PCT Filed: Nov. 7, 2008

(86) PCT No.: PCT/GB2008/051042
§ 371 (c)(1),
(2), (4) Date: Aug. 17, 2010

(87) PCT Pub. No.: WO2009/060242
PCT Pub. Date: May 14, 2009

(65) Prior Publication Data
US 2010/0301129 A1    Dec. 2, 2010

Related U.S. Application Data

(60) Provisional application No. 60/989,083, filed on Nov. 19, 2007, provisional application No. 60/987,021, filed on Nov. 9, 2007.

(30) Foreign Application Priority Data

Mar. 3, 2008 (GB) .................................. 0803959.6

(51) Int. Cl.
*A62C 5/00* (2006.01)
*A62C 31/07* (2006.01)
(Continued)

(52) U.S. Cl.
CPC . *A62C 31/07* (2013.01); *A61L 2/22* (2013.01); *A61L 2202/25* (2013.01); *A62C 5/008* (2013.01);
(Continued)

(58) Field of Classification Search
CPC ...... B05B 7/066; B05B 7/065; B05B 7/0466; B05B 7/067; B05B 7/0475; A62C 31/07; A62C 99/0072; A62C 5/008; A61L 2202/25; A61L 2/22

USPC ........... 239/433, 10, 398, 418, 421, 423, 424, 239/424.5, 425, 434.5, 310, 311
See application file for complete search history.

(56) References Cited

U.S. PATENT DOCUMENTS 1,779,680 A    10/1930    Rayfield
2,990,885 A    7/1961    Brazier
(Continued)

FOREIGN PATENT DOCUMENTS

WO    WO 94/08724 A    4/1994
WO    WO 01/76764 A    10/2001
(Continued)

OTHER PUBLICATIONS

International Searching Authority, International Search Report and Written Opinion issued in International Application No. PCT/GB2008/051042, Mar. 5, 2009, 8 pages.
(Continued)

*Primary Examiner* — Jason Boeckmann
(74) *Attorney, Agent, or Firm* — Perkins Coie LLP

(57) ABSTRACT

A decontaminating system (100) comprising a decontaminant reservoir (152), a transport fluid source (160) and a mist generating apparatus (10). The mist generating apparatus (10) has a longitudinal axis and comprises a first fluid passage (38) having a first fluid inlet (18) in fluid communication with the decontaminant reservoir (152) and a first fluid outlet (84), and a second fluid passage (90) having a second fluid inlet (20) in fluid communication with the transport fluid source (160) and a second fluid outlet (94). The first passage (38) surrounds the second fluid passage (90) and the first and second outlets (84, 94) are oriented relative to one another such that they have an angle of incidence between (5) and (30) degrees. The second fluid passage (90) includes a throat portion (92) located between the second fluid inlet (20) and the second fluid outlet (94), the throat portion (92) having a smaller cross sectional area than that of either the second fluid inlet (20) or second fluid outlet (94).

36 Claims, 11 Drawing Sheets

(51) Int. Cl.
  *A61L 2/22* (2006.01)
  *A62C 99/00* (2010.01)
  *B05B 7/04* (2006.01)
  *B05B 7/06* (2006.01)

(52) U.S. Cl.
  CPC ........... *A62C 99/0072* (2013.01); *B05B 7/0433* (2013.01); *B05B 7/0466* (2013.01); *B05B 7/0475* (2013.01); *B05B 7/065* (2013.01); *B05B 7/067* (2013.01)

(56) References Cited

U.S. PATENT DOCUMENTS

| | | | |
|---|---|---|---|
| 3,073,534 | A | 1/1963 | Hampshire |
| 3,684,188 | A | 8/1972 | Miller et al. |
| 4,337,618 | A | 7/1982 | Hughes et al. |
| 4,634,054 | A | 1/1987 | Grusha |
| 4,903,895 | A * | 2/1990 | Mathewson et al. ......... 239/14.2 |
| RE33,464 | E * | 11/1990 | Gitman ........................... 432/13 |
| 5,176,324 | A * | 1/1993 | Furuse et al. .................. 239/419 |
| 5,462,229 | A * | 10/1995 | Tanaka et al. ............... 239/397.5 |
| 6,405,944 | B1 | 6/2002 | Benalikhoudja |
| 6,662,549 | B2 * | 12/2003 | Burns ............................. 60/204 |
| 7,967,221 | B2 * | 6/2011 | Snyder et al. ................. 239/418 |
| 2006/0102749 | A1 * | 5/2006 | Crabtree et al. .............. 239/410 |
| 2007/0210186 | A1 | 9/2007 | Fenton et al. |
| 2008/0230632 | A1 | 9/2008 | Fenton et al. |
| 2009/0314500 | A1 * | 12/2009 | Fenton et al. .................. 169/16 |
| 2010/0230119 | A1 | 9/2010 | Worthy et al. |
| 2011/0127347 | A1 | 6/2011 | Worthy et al. |
| 2011/0203813 | A1 | 8/2011 | Fenton et al. |
| 2012/0018531 | A1 | 1/2012 | Fenton et al. |

FOREIGN PATENT DOCUMENTS

| | | |
|---|---|---|
| WO | WO 03/072952 A | 9/2003 |
| WO | WO 2005/082546 A | 9/2005 |

OTHER PUBLICATIONS

International Searching Authority, International Preliminary Report on Patentability issued in International Application No. PCT/GB2008/051042, May 11, 2010, 6 pages.
U.S. Appl. No. 10/590,456 (Publication No. 2007-0210186 A1) Co-Pending Related U.S. Appl. No. 12/741,941.
U.S. Appl. No. 10/590,527 (Publication No. 2008-0230632 A1) Co-Pending Related U.S. Appl. No. 12/741,941.
U.S. Appl. No. 12/381,584 (Publication No. 2009-0314500 A1) Co-Pending Related U.S. Appl. No. 12/741,941.
U.S. Appl. No. 12/741,995 (Publication No. 2012-0018531 A1) Co-Pending Related U.S. Appl. No. 12/741,941.
U.S. Appl. No. 12/742,046 (Publication No. 2011-0203813 A1) Co-Pending Related U.S. Appl. No. 12/741,941.
U.S. Appl. No. 12/592,930 (Publication No. 2010-0230119 A1) Co-Pending Related U.S. Appl. No. 12/741,941.
U.S. Appl. No. 12/996,348 (Publication No. 2011-0127347 A1) Co-Pending Related U.S. Appl. No. 12/741,941.
European Application No. 08848325.0, Nov. 26, 2013 from the EPO Patent Register.
Examination Report issued in related co-pending Australian Application No. 2008326236, Jun. 19, 2013, 3 pages.
Response to Jun. 19, 2012 Examination Report in related Australian Application No. 2008326236, Dec. 18, 2013, 32 pages.
Australian Application No. 2008326236, Nov. 25, 2014 from AUSPAT Australian Patent Office.

* cited by examiner

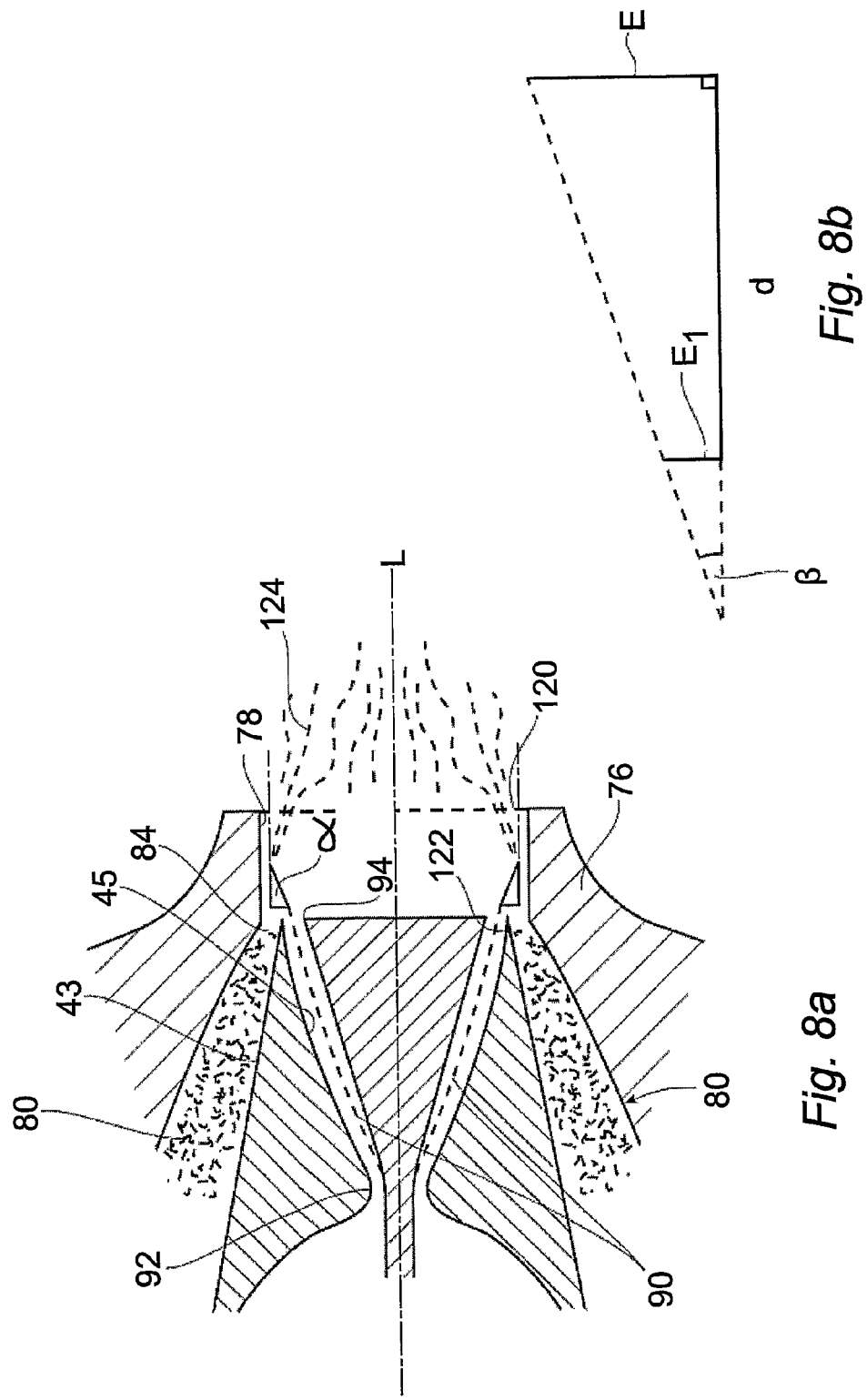

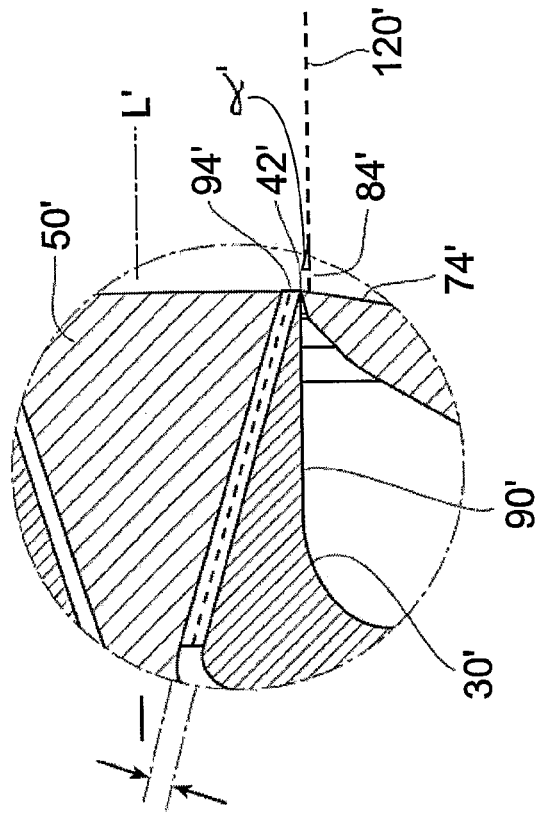
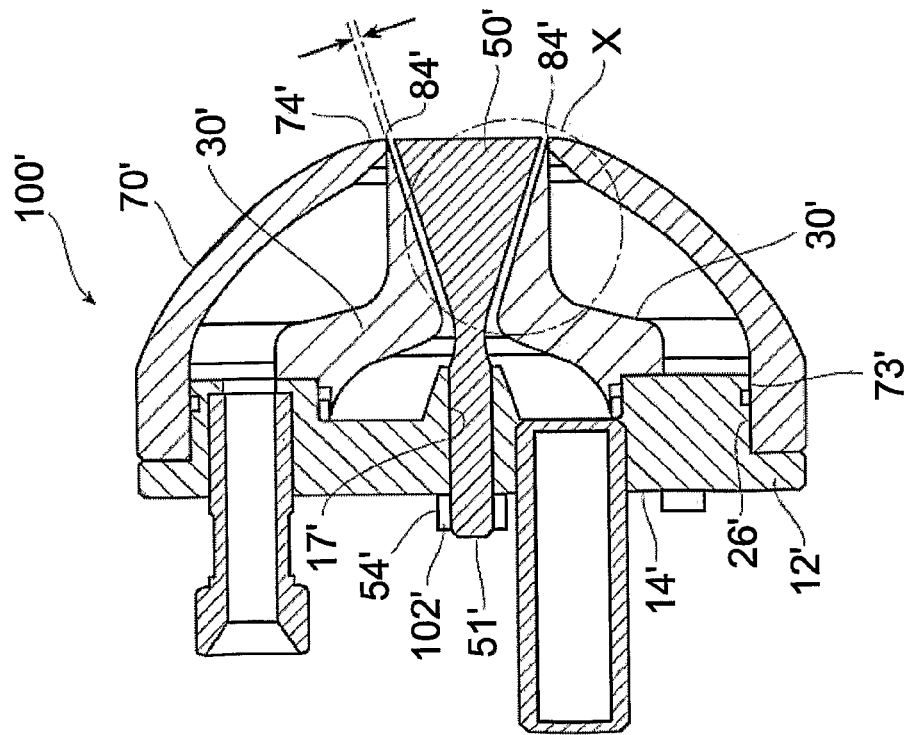
Fig. 10
Fig. 9

DECONTAMINATION

This application is a U.S. National Stage Application of International Application No. PCT/GB2008/051042, which was filed on Nov. 7, 2008, and which claims priority to U.S. Provisional Application No. 60/987,021, which was filed on Nov. 9, 2007, U.S. Provisional Application No. 60/989,083, which was filed on Nov. 19, 2007, and Great Britain Application No. 0803959.6, which was filed on Mar. 3, 2008, all of which are incorporated by reference in their entireties as if recited in full herein.

The present invention is concerned with decontamination. More specifically, the present invention is directed towards a method and system for generating a decontaminating mist.

WO01/76764 shows a mist generating apparatus which uses two fluids, primarily for use in fire suppression. In WO'764 a spray of first fluid droplets is created by forcing the first fluid through a number of aerosol nozzles in a conventional manner. The droplets are then carried by a stream of a second fluid through a convergent-divergent nozzle which sprays the combined stream of first fluid droplets and second fluid from the apparatus. The purpose of WO '764 is to reduce the pressure required to create the aerosol spray of the first fluid by using the second stream of fluid to carry the first fluid droplets out of the apparatus. The second stream also reduces frictional forces which can, in some cases, cause the first fluid droplets forming the aerosol spray to evaporate.

WO '764 does not use the second fluid in order to create the first fluid droplet regime. Instead, the droplets are created via an array of aerosol nozzles which create the droplets in a conventional manner. The stream of second fluid then carries the droplets through the spray nozzle without any atomisation mechanism being applied to the first fluid by the second fluid. Thus, WO'764 still requires the first fluid to be supplied at relatively high pressure in order to create the aerosol droplets.

It is an aim of the present invention to obviate or mitigate one or more of the aforementioned disadvantages.

According to a first aspect of the present invention, there is provided a decontaminating system comprising:
a decontaminant reservoir;
a transport fluid source; and
a mist generating apparatus having a longitudinal axis, the apparatus comprising:
a first fluid passage having a first fluid inlet in fluid communication with the decontaminant reservoir and a first fluid outlet;
a second fluid passage having a second fluid inlet in fluid communication with the transport fluid source and a second fluid outlet,
wherein the first fluid passage surrounds the second fluid passage, and the first and second outlets are oriented relative to one another such that they have an angle of incidence between 5 and 30 degrees; and
the second fluid passage includes a throat portion located between the second fluid inlet and the second fluid outlet, the throat portion having a smaller cross sectional area than that of either the second fluid inlet or second fluid outlet.

Preferably, the area ratio between the throat portion and the second fluid outlet is between 2:3 and 1:4.

Preferably, the first and second passages are coaxial with the longitudinal axis of the apparatus.

Preferably, the second fluid outlet has a cross sectional area which is between 1.4 and 5.5 times larger than the cross sectional area of the throat portion.

Preferably, the first fluid passage has a cross sectional area which converges between the first fluid inlet and the first fluid outlet.

Preferably, the first fluid passage includes an intermediate portion located between the first fluid inlet and the first fluid outlet, the intermediate portion having a cross sectional area which is larger than that of either the first fluid inlet or the first fluid outlet.

Preferably, the mist generating apparatus is configured to accelerate the flow of transport fluid through the second fluid passage. More preferably, the second fluid passage includes a converging-diverging portion and the flow of transport fluid is accelerated through the converging-diverging portion.

Preferably, the mist generating apparatus is configured such that the decontaminant fluid and transport fluid are ejected from their respective outlets such that a stream of accelerated transport fluid issuing from the second fluid outlet imparts a shear force on a stream of decontaminant fluid issuing from the first fluid outlet, thereby at least partially atomising the decontaminant fluid to form a dispersed droplet flow regime.

Preferably, the mist generating apparatus is configured such that a turbulent region of the transport fluid is created downstream of the outlets and the dispersed droplet flow regime is passed through the turbulent region to further atomise the dispersed droplet flow regime.

The cross sectional area of the throat portion may be between 20 and 35 mm$^2$. The equivalent angle of expansion of the second fluid passage between the throat and the second fluid outlet may be between 5 and 10 degrees. The cross sectional area of the second fluid outlet may be between 4 and 7 times larger than the cross sectional area of the first fluid outlet.

Preferably, the mist generating apparatus further comprises a first fluid supply channel having a first end adapted to be connected to the decontaminant reservoir and a second end connected to the first fluid inlet, and a second fluid supply channel having a first end adapted to be connected to the transport fluid source and a second end connected to the second fluid inlet, wherein the first and second supply channels are substantially parallel to the longitudinal axis of the apparatus.

Preferably, the mist generating apparatus is configured such that the momentum flux ratio between the decontaminant fluid and transport fluid may be controlled by varying the density and/or velocity of the decontaminant fluid and/or transport fluid.

Preferably, the mist generating apparatus is configured such that the cross sectional area of the first fluid outlet is adjustable such that the exit velocity of the decontaminant fluid stream may be varied.

Preferably, the mist generating apparatus is configured such that the at least partial atomisation of the decontaminant fluid takes place at least partially within the mist generating apparatus.

Preferably, the first and second outlets may be located adjacent one another.

Preferably, the mist generating apparatus comprises a base member that contains the first and second supply channels.

The mist generating apparatus may further comprise a funnel member and an elongate plug member, wherein the funnel member has a bore and is adapted to coaxially locate upon the base such that the bore communicates with the second fluid supply channel, and wherein the plug member is adapted to be attached to the base member such that a portion of the plug lies within the bore and the second fluid passage is defined between the funnel and the plug.

The mist generating apparatus may further comprise a cover member which encloses the base member, the funnel member and the plug member such that the first fluid passage is defined between an outer surface of the funnel and an inner surface of the cover member. The cover may have a first end adapted to coaxially locate upon the base member and be attached thereto, and a second end having an outlet adapted to communicate with the first and second fluid outlets.

The second end of the cover may include an axially projecting lip portion, the lip portion defining an aperture in communication with the first and second fluid outlets.

The plug member may have a first end which attaches to the base member and a second end which defines the second fluid passage, wherein the second end is concave.

The funnel member may include a radially projecting flange portion, wherein the flange portion is sandwiched between the base member and the cover member to maintain the axial position of the funnel member relative to the base member.

The cover member may be threaded onto the base such that the axial position of the cover member may be adjusted relative to the base.

The plug member may be threaded onto the base such that the axial position of the plug member may be adjusted relative to the base and the funnel.

Preferably, the system further comprises a plurality of mist generating apparatuses. The plurality of mist generating apparatuses may be connected in series and/or in parallel to form an array.

Preferably, the decontaminant reservoir includes an outlet controlled by an outlet valve.

The system may further comprise first pressurising means for pressurising the decontaminant fluid in the decontaminant reservoir. Alternatively, the decontaminant fluid may be stored under pressure in the decontaminant reservoir.

The system may further comprise a pump or compressor for transporting the decontaminant fluid from the decontaminant reservoir to the mist generating apparatus. The pump or compressor may be controlled by a programmable system controller. The compressor may draw air from the atmosphere.

The system may further comprise pressure regulation means for regulating the pressure of the decontaminant fluid in the decontaminant reservoir.

The system may further comprise flow rate regulation means for regulating the flow rate of the decontaminant fluid between the decontaminant reservoir and the mist generating apparatus.

Preferably, the transport fluid source may include an outlet controlled by an outlet valve.

Preferably, the system may further comprise second pressurising means for pressurising the transport fluid in the transport fluid source. Alternatively, the transport fluid may be stored under pressure in the transport fluid source.

The system may further comprise a pump, or compressor, for pumping the transport fluid from the transport fluid source to the mist generating apparatus. The pump, or compressor, may be controlled by a programmable system controller.

The system may further comprise pressure regulation means for regulating the pressure of the transport fluid in the transport fluid source.

The system may further comprise flow rate regulation means for regulating the flow rate of the transport fluid between the transport fluid source and the mist generating apparatus.

The system may further comprise remote operating means such that the mist generating apparatus, or apparatuses, may be operated and controlled remotely.

The system may further comprise one or more sensors which are capable of sensing one or more decontaminants.

The system may further comprise a power supply.

Preferably, the system is portable. More preferably, the system is mounted on a portable frame. The portable frame may include ground engaging wheel means. The portable frame may include vehicle engaging means such that the system may be towed by a vehicle. The ground engaging wheel means may be operable remotely.

According to a second aspect of the present invention, there is provided a decontaminating system comprising:
 a decontaminant reservoir;
 a transport fluid source; and
 a mist generating apparatus having a longitudinal axis, the apparatus comprising:
 a first fluid passage having a first fluid inlet in fluid communication with the decontaminant reservoir and a first fluid outlet;
 a second fluid passage having a second fluid inlet in fluid communication with the transport fluid source and a second fluid outlet,
 wherein the first fluid passage surrounds the second fluid passage, and the first and second outlets are oriented relative to one another such that they have an angle of incidence of less than 90 degrees; and
 the second fluid passage includes a throat portion located between the second fluid inlet and the second fluid outlet, the throat portion having a smaller cross sectional area than that of either the second fluid inlet or second fluid outlet such that area ratio between the throat portion and the second fluid outlet is between 2:3 and 1:4

Preferably, the first and second passages are coaxial with the longitudinal axis of the apparatus.

Preferably, the second fluid outlet has a cross sectional area which is between 1.4 and 5.5 times larger than the cross sectional area of the throat portion.

Preferably, the first fluid passage has a cross sectional area which converges between the first fluid inlet and the first fluid outlet.

Preferably, the first fluid passage includes an intermediate portion located between the first fluid inlet and the first fluid outlet, the intermediate portion having a cross sectional area which is larger than that of either the first fluid inlet or the first fluid outlet.

Preferably, the mist generating apparatus is configured to accelerate the flow of transport fluid through the second fluid passage. More preferably, the second fluid passage includes a converging-diverging portion and the flow of transport fluid is accelerated through the converging-diverging portion.

Preferably, the mist generating apparatus is configured such that the decontaminant fluid and transport fluid are ejected from their respective outlets such that a stream of accelerated transport fluid issuing from the second fluid outlet imparts a shear force on a stream of decontaminant fluid issuing from the first fluid outlet, thereby at least partially atomising the decontaminant fluid to form a dispersed droplet flow regime.

Preferably, the mist generating apparatus is configured such that a turbulent region of the transport fluid is created downstream of the outlets and the dispersed droplet flow regime is passed through the turbulent region to further atomise the dispersed droplet flow regime.

The cross sectional area of the throat portion may be between 20 and 35 $mm^2$. The equivalent angle of expansion of the second fluid passage between the throat and the second fluid outlet may be between 5 and 10 degrees. The cross sectional area of the second fluid outlet may be between 4 and 7 times larger than the cross sectional area of the first fluid outlet.

Preferably, the mist generating apparatus further comprises a first fluid supply channel having a first end adapted to be connected to the decontaminant reservoir and a second end connected to the first fluid inlet, and a second fluid supply channel having a first end adapted to be connected to the transport fluid source and a second end connected to the second fluid inlet, wherein the first and second supply channels are substantially parallel to the longitudinal axis of the apparatus.

Preferably, the mist generating apparatus is configured such that the momentum flux ratio between the decontaminant fluid and transport fluid may be controlled by varying the density and/or velocity of the decontaminant fluid and/or transport fluid.

Preferably, the mist generating apparatus is configured such that the cross sectional area of the first fluid outlet is adjustable such that the exit velocity of the decontaminant fluid stream may be varied.

Preferably, the mist generating apparatus is configured such that the at least partial atomisation of the decontaminant fluid takes place at least partially within the mist generating apparatus.

Preferably, the first and second outlets may be located adjacent one another.

Preferably, the mist generating apparatus comprises a base member that contains the first and second supply channels.

The mist generating apparatus may further comprise a funnel member and an elongate plug member, wherein the funnel member has a bore and is adapted to coaxially locate upon the base such that the bore communicates with the second fluid supply channel, and wherein the plug member is adapted to be attached to the base member such that a portion of the plug lies within the bore and the second fluid passage is defined between the funnel and the plug.

The mist generating apparatus may further comprise a cover member which encloses the base member, the funnel member and the plug member such that the first fluid passage is defined between an outer surface of the funnel and an inner surface of the cover member. The cover may have a first end adapted to coaxially locate upon the base member and be attached thereto, and a second end having an outlet adapted to communicate with the first and second fluid outlets.

The second end of the cover may include an axially projecting lip portion, the lip portion defining an aperture in communication with the first and second fluid outlets.

The plug member may have a first end which attaches to the base member and a second end which defines the second fluid passage, wherein the second end is concave.

The funnel member may include a radially projecting flange portion, wherein the flange portion is sandwiched between the base member and the cover member to maintain the axial position of the funnel member relative to the base member.

The cover member may be threaded onto the base such that the axial position of the cover member may be adjusted relative to the base.

The plug member may be threaded onto the base such that the axial position of the plug member may be adjusted relative to the base and the funnel.

Preferably, the system further comprises a plurality of mist generating apparatuses. The plurality of mist generating apparatuses may be connected in series and/or in parallel to form an array.

Preferably, the decontaminant reservoir includes an outlet controlled by an outlet valve.

The system may further comprise first pressurising means for pressurising the decontaminant fluid in the decontaminant reservoir. Alternatively, the decontaminant fluid may be stored under pressure in the decontaminant reservoir.

The system may further comprise a pump or compressor for transporting the decontaminant fluid from the decontaminant reservoir to the mist generating apparatus. The pump or compressor may be controlled by a programmable system controller. The compressor may draw air from the atmosphere.

The system may further comprise pressure regulation means for regulating the pressure of the decontaminant fluid in the decontaminant reservoir.

The system may further comprise flow rate regulation means for regulating the flow rate of the decontaminant fluid between the decontaminant reservoir and the mist generating apparatus.

Preferably, the transport fluid source may include an outlet controlled by an outlet valve.

Preferably, the system may further comprise second pressurising means for pressurising the transport fluid in the transport fluid source. Alternatively, the transport fluid may be stored under pressure in the transport fluid source.

The system may further comprise a pump, or compressor, for pumping the transport fluid from the transport fluid source to the mist generating apparatus. The pump, or compressor, may be controlled by a programmable system controller.

The system may further comprise pressure regulation means for regulating the pressure of the transport fluid in the transport fluid source.

The system may further comprise flow rate regulation means for regulating the flow rate of the transport fluid between the transport fluid source and the mist generating apparatus.

The system may further comprise remote operating means such that the mist generating apparatus, or apparatuses, may be operated and controlled remotely.

The system may further comprise one or more sensors which are capable of sensing one or more decontaminants.

The system may further comprise a power supply.

Preferably, the system is portable. More preferably, the system is mounted on a portable frame. The portable frame may include ground engaging wheel means. The portable frame may include vehicle engaging means such that the system may be towed by a vehicle. The ground engaging wheel means may be operable remotely.

According to a third aspect of the present invention, there is provided a method of generating a decontaminating mist, the method comprising:

passing a decontaminant fluid through a first fluid passage of a mist generating apparatus, wherein the first fluid passage has a first fluid outlet;

passing a transport fluid through a second fluid passage of the mist generating apparatus, wherein the second fluid passage has a second fluid outlet and a throat portion, the throat portion having a smaller cross sectional area than the second fluid outlet, wherein the first and second outlets are oriented relative to one another such that they have an angle of incidence between 5 and 30 degrees;

accelerating the flow of transport fluid through the throat portion of the second fluid passage; and ejecting the decontaminant and transport fluids from their respective outlets such that a stream of accelerated transport fluid issuing from the second fluid outlet imparts a shear force on a stream of decontaminant fluid issuing from the first fluid outlet, thereby at least partially atomising the decontaminant fluid to create a dispersed droplet flow regime.

Preferably, the method comprises the further step of creating a turbulent region in the transport fluid downstream of the outlets; and passing the dispersed droplet flow regime through the turbulent region, thereby further atomising the dispersed droplet flow regime.

Preferably, the method comprises the further step of controlling the momentum flux ratio between the decontaminant fluid and the transport fluid by varying the velocity and/or density of the decontaminant fluid and the transport fluid.

Preferably, the method comprises the further step of adjusting the cross sectional area of the first fluid outlet in order to vary the exit velocity of the decontaminant fluid stream.

Preferably, the exit velocity is supersonic.

Preferably, the second fluid outlet has a cross sectional area which is between 1.4 and 5.5 times larger than the cross sectional area of the throat portion.

Preferably, the transport fluid may be compressible. The transport fluid may be a gas. The gas may be air, Nitrogen or Helium, alternatively, carbon dioxide or steam.

The at least partial atomisation of the decontaminant fluid may take place at least partially within the mist generating apparatus.

According to a fourth aspect of the present invention, there is provided a method of generating a decontaminating mist, the method comprising:

passing a decontaminant fluid through a first fluid passage of a mist generating apparatus, wherein the first fluid passage has a first fluid outlet;

passing a transport fluid through a second fluid passage of the mist generating apparatus, wherein the second fluid passage has a second fluid outlet and a throat portion, the throat portion having a smaller cross sectional area than the second fluid outlet such that the area ratio between the throat portion and the second fluid outlet is between 2:3 and 1:4, wherein the first and second fluid outlets are oriented relative to one another such that they have an angle of incidence of less than 90 degrees;

accelerating the flow of transport fluid through the throat portion of the second fluid passage; and ejecting the decontaminant and transport fluids from their respective outlets such that a stream of accelerated transport fluid issuing from the second fluid outlet imparts a shear force on a stream of decontaminant fluid issuing from the first fluid outlet, thereby at least partially atomising the decontaminant fluid to create a dispersed droplet flow regime.

Preferably, the method comprises the further step of creating a turbulent region in the transport fluid downstream of the outlets; and passing the dispersed droplet flow regime through the turbulent region, thereby further atomising the dispersed droplet flow regime.

Preferably, the method comprises the further step of controlling the momentum flux ratio between the decontaminant fluid and the transport fluid by varying the velocity and/or density of the decontaminant fluid and the transport fluid.

Preferably, the method comprises the further step of adjusting the cross sectional area of the first fluid outlet in order to vary the exit velocity of the decontaminant fluid stream.

Preferably, the exit velocity is supersonic.

Preferably, the second fluid outlet has a cross sectional area which is between 1.4 and 5.5 times larger than the cross sectional area of the throat portion.

Preferably, the transport fluid may be compressible. The transport fluid may be a gas. The gas may be air, Nitrogen or Helium, alternatively, carbon dioxide or steam.

The at least partial atomisation of the decontaminant fluid may take place at least partially within the mist generating apparatus.

According to a fifth aspect of the present invention, there is provided a method for decontaminating an enclosed space including the method according to the third or fourth aspect of the invention.

According to a sixth aspect of the present invention, there is provided a system for decontaminating an enclosed space, wherein the system includes the decontaminating system according to the first or second aspect of the invention.

According to a seventh aspect of the present invention, there is provided a decontamination room or enclosure including a decontaminating system according to the first or second aspect of the invention.

A preferred embodiment of the invention will now be described, by way of example only, with reference to the accompanying drawings, in which:

FIG. 8a is a schematic sectional view of the operation of the apparatus shown in FIG. 5;

FIG. 8b is a schematic view of the geometry of the second fluid passage of the apparatus shown in FIG. 5;

FIG. 9 is a longitudinal section view of an alternative embodiment of the mist-generating apparatus;

FIG. 10 is a detail view of the area marked "X" in FIG. 9;

Figure 1:
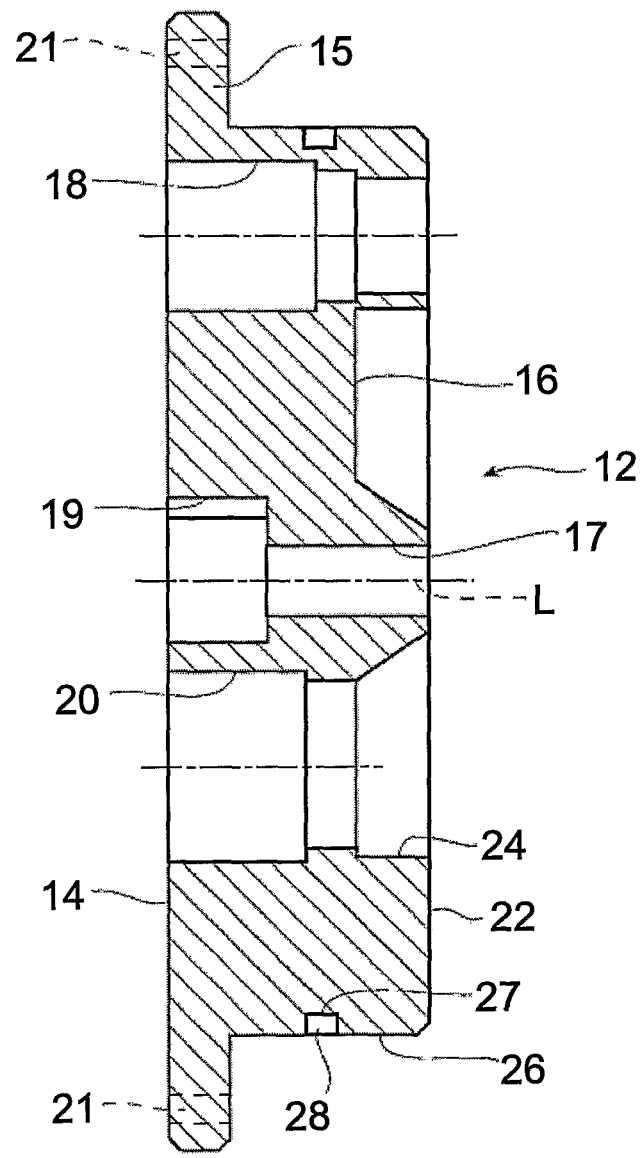
FIG. 1 shows a longitudinal section view through a base of a mist-generating apparatus.

FIG. 1 is a longitudinal section view through a mist generating apparatus 10 used in accordance with the present invention. The apparatus 10 has a generally circular base 12, a rear face 14, a front face 16 and first and second fluid inlet passages 18, 20 adapted to receive the decontaminating fluid and transport fluid from their respective sources (not shown). Each of the fluid inlet passages 18, 20 are substantially parallel with the longitudinal axis L of the apparatus. Each fluid inlet passage 18, 20 has an internal thread adapted to receive the external thread of respective fluid supply channels (not shown). Extending longitudinally through the centre of the base 12 is a bore 17. The bore 17 has a generally triangular-shaped recess 19 opening on the rear face 14 of the base 12. The base 12 includes a radially extending flange portion 15 and an axially projecting annular projection 22 which projects forwards from the front face 16. A plurality of circumferentially spaced apertures 21 extend longitudinally through the flange portion 15. The annular projection 22 has an inner surface 24 and an outer surface 26. The outer surface 26 contains a groove 27 in which an O-ring seal 28 is located.

Figure 2:
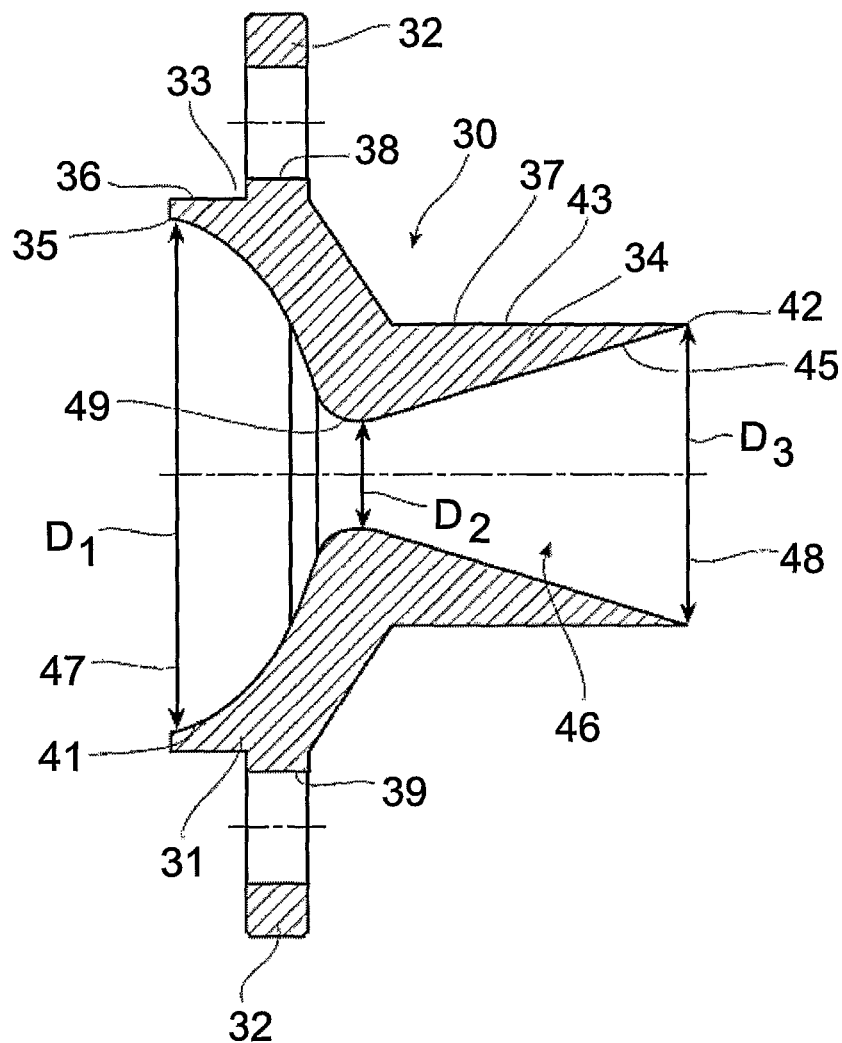
FIG. 2 shows a longitudinal section view through a funnel of a mist-generating apparatus.

FIG. 2 shows a projecting member, funnel, 30 which also forms part of the mist generating apparatus 10. The funnel 30 is preferably formed as a single piece and comprises a radially extending flange portion 32 and an axially projecting body portion 34. The body portion 34 has an outer surface 37. An annular lip portion 31 extends rearwards from the flange portion 32 and defines an outer surface 33. The outer surface 33 contains a groove 35 in which an O-ring seal 36 is located. The flange portion 32 is annular and extends around the entire circumference of the projecting member 30. Defined within the flange portion 32 are a first fluid passage 38 and an inspection port 39.

The funnel 30 has a first end 41 and a second end 42 and a bore 46 extending longitudinally through the funnel 30 from the first end 41 to the second end 42. The bore 46 has an inlet 47 at the first end 41, an outlet 48 at the second end 42, and a throat portion 49 intermediate the inlet 47 and outlet 48. The bore 46 may have an axial length of between 52 mm and 55 mm. At the inlet 47 the bore 46 has a diameter D1 which may be between 53 mm and 59 mm. At the throat portion 49 the diameter of the bore 46 is D2 which may be between 7.5 mm and 13 mm, and at the outlet 48 the diameter of the bore is D3 which may be between 30 mm and 34 mm. The diameter D1 at the inlet 47 is greater than the diameter D2 or D3, whilst the diameter D2 at the throat portion 49 is less than the diameters D1 and D3. As a result, the bore 46 narrows from its widest point at the inlet 47 to a narrow diameter at the throat portion 49 before widening again until it reaches the outlet 48.

Figure 3:
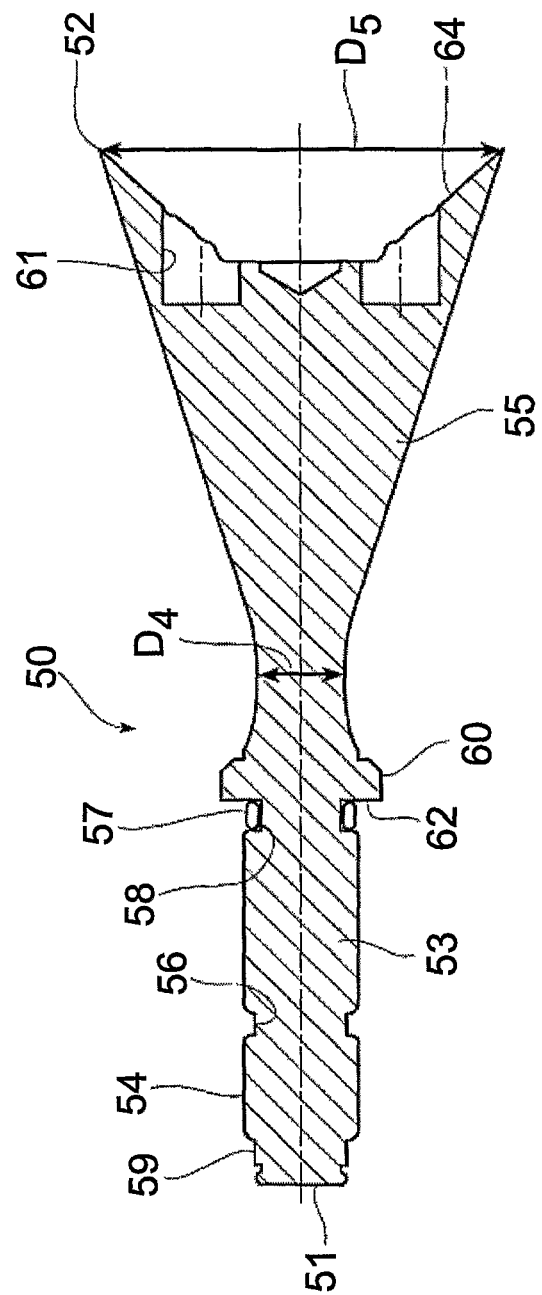
FIG. 3 shows a longitudinal section view through a plug of a mist-generating apparatus.

FIG. 3 shows a plug 50 forming a further part of the mist generating apparatus 10. The plug 50 is an elongate member having a first end 51 and a second end 52. The plug 50 has a first generally cylindrical portion 53 and a second conical portion 55 extending from, and preferably integrally formed with, the cylindrical portion 53. Part of the cylindrical portion 53 adjacent the first end 51 is provided with an external thread 54.

The conical portion 55 is in the shape of an inverted cone, with the narrowest point of the cone adjacent the cylindrical portion 53 and the widest point of the cone at the second end 52 of the plug 50. The conical portion 55 has a smallest diameter D4 adjacent the cylindrical portion 53 and a largest diameter D5 at the second end 52 of the plug 50. The cylindrical portion 53 has first and second grooves 56, 58 longitudinally spaced from one another and extending around the circumference of the cylindrical portion 53. The first groove 56 is a thread relief groove co-operating with the external thread 54. Also formed part way along the cylindrical portion 53 is a radially projecting lip 60, which defines an abutment surface 62 facing towards the first end 51 of the plug 50. The second groove 58 holds an O-ring seal 57. A further groove 59 is provided in the cylindrical portion 53 of the plug 50 adjacent the first end 51.

The second end 52 of the plug 50, which is also the widest part of the conical portion 55, has an end face which is concave. Thus, a dish-shaped cavity 64 is formed in the second end face of the plug 50. The end face of the second end 52 also includes a pair of locating holes 61.

Figure 4:
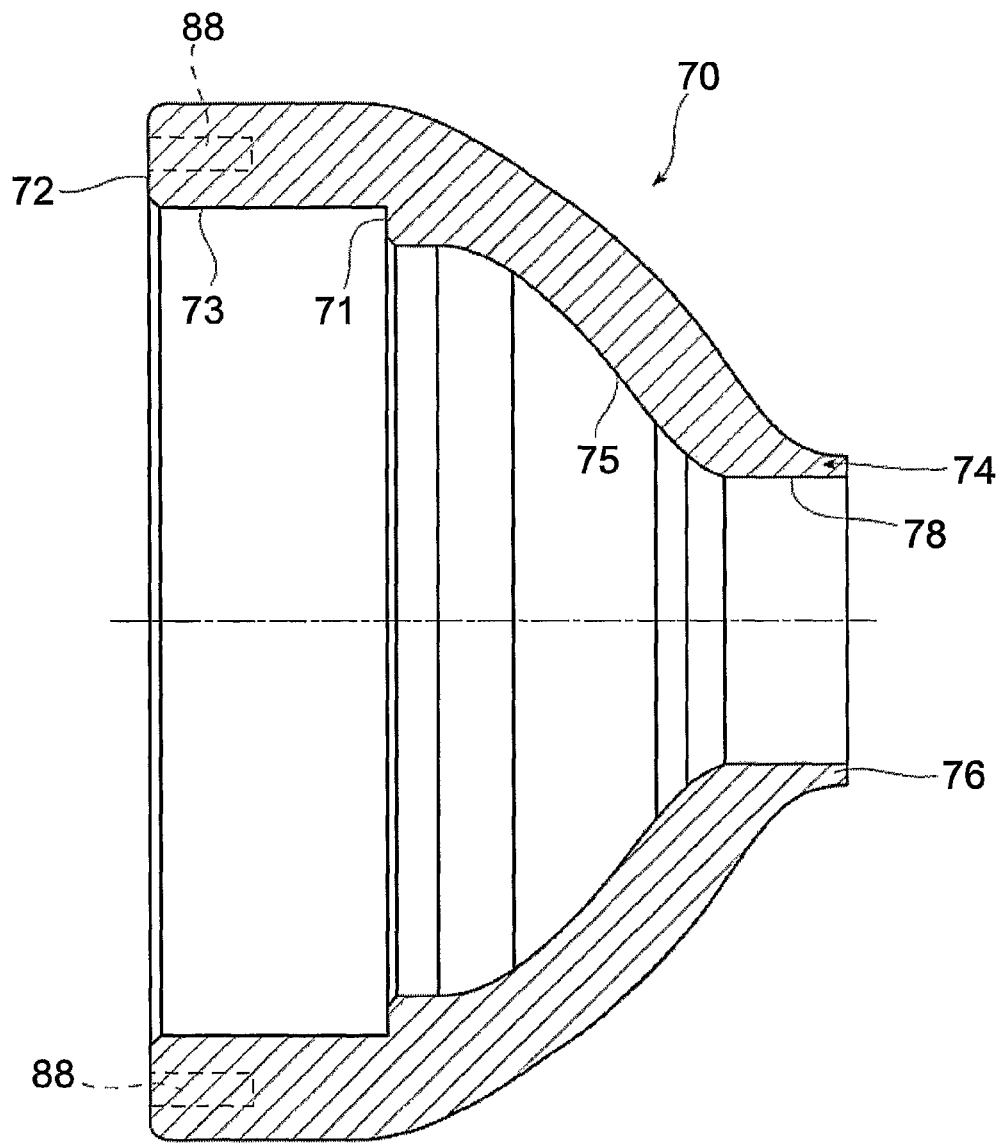
FIG. 4 shows a longitudinal section view through a cover of a mist-generating apparatus.

FIG. 4 shows a cover 70 forming part of the mist generating apparatus 10. The cover 70 is generally dome-shaped, having a first end 72 of larger diameter than a second end 74. Projecting axially from the second end 74 of the cover 70 is an annular lip 76. The lip 76 has an internal surface 78 which defines a bore of substantially constant diameter. In other words, the lip 76 has internal walls which are substantially parallel when viewed in vertical cross-section, such as here in FIG. 4. The cover 70 has a first section adjacent the first end 72 which has a first inner surface 73 of substantially constant diameter. Located in the first end 72 of the cover 70 at circumferentially spaced intervals are a plurality of axially extending threaded holes 88. A second section of the cover 70 extending between the first section and the lip 76 has a second inner surface 75. The portion of the second section adjoining the first section has a smaller diameter than that of the first section, such that a rearward facing abutment 71 is defined between the first and second sections of the cover 70. The diameter of the second section reduces in the direction of the second end 74. In other words, the second inner surface 75 tapers inwardly from the abutment 71 until it reaches the internal surface 78 of the lip 76. Thus, the second inner surface 75 has a smooth inwardly curving profile as it progresses towards the second end 74, with no steps or angles present on the inner surface 75.

The manner in which the mist-generating apparatus 10 is assembled will now be described. Firstly, each of the components detailed above are formed from a suitable material, which is preferably stainless steel. In the first step of assembling the apparatus 10, the funnel 30 is axially inserted onto the base 12 so that the base 12 and funnel 30 are concentric about the longitudinal axis L, with the outer surface 33 of the funnel lip 31 being guided by the inner surface 24 of the annular projection 22, until the rear face of the flange portion 32 abuts the surface of the annular projection 22. The O-ring seal 36 located in the groove 35 on the outer surface 33 ensures a sealing fit between the two components. When the base 12 and funnel 30 are correctly positioned, the first fluid inlet passage 18 of the base 12 and first fluid passage 38 of the funnel are aligned and capable of fluid communication with one another. Furthermore, the inlet 47 of the funnel bore 46 and the second fluid inlet passage 20 of the base 12 are now in fluid communication with one another as well. Once the base 12 and funnel 30 have been correctly oriented with respect to one another, a temporary locking ring (not shown) is secured over the flange portion 32 of the funnel 30 such that the base 12 and funnel 30 are locked together.

Figure 6:
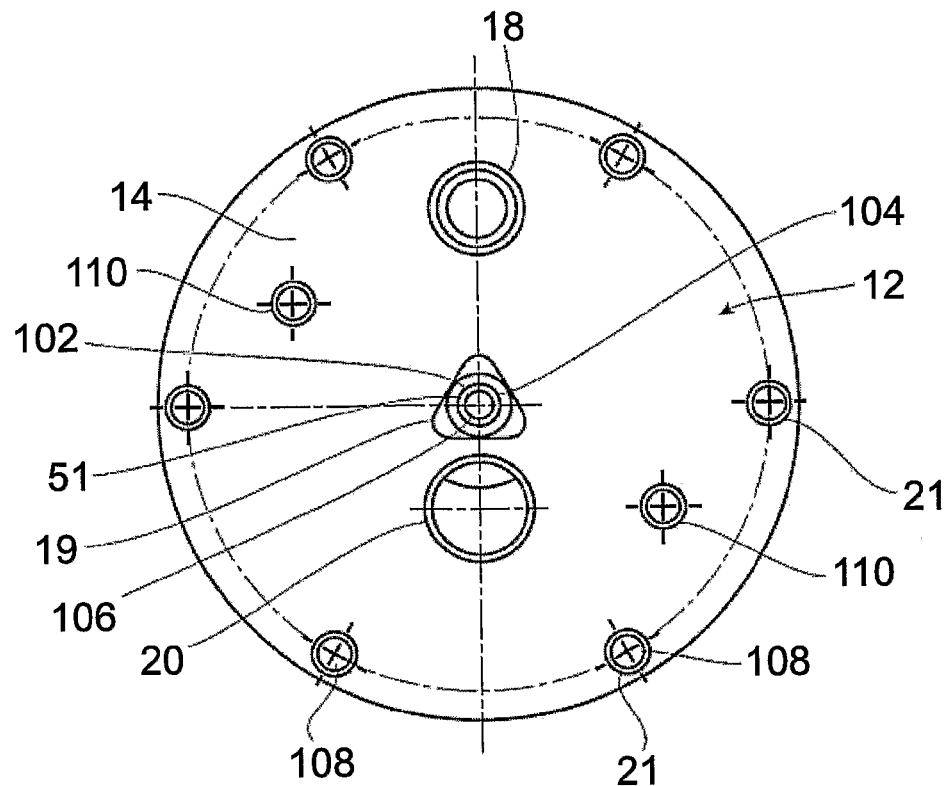
FIG. 6 is an end view of the apparatus shown in FIG. 5.

Once the base 12 and funnel 30 are temporarily locked together, the plug 50 can be introduced, firstly via the bore 46 of the funnel 30 and then the bore 17 of the base 12. As best seen in FIG. 6, a locking nut 102 is inserted into the recess 19. As the plug 50 is inserted through the bores 46, 17 it is rotated by a suitable tool (not shown) which locates in the locating holes 61. As the plug 50 is rotated the threaded surface 54 of the plug 50 marries with the internal thread of the locking nut 102. The outer faces of the nut 102 contact the inner surfaces of the triangular recess 19 such that the recess 19 prevents the nut 102 from rotating as the first end 51 and threaded surface 54 of the plug 50 are threaded through. The lip 60 of the plug 50 has a larger diameter than the bore 17. Consequently, once the abutment surface 62 of the lip 60 comes into contact with the base 12, the plug 50 cannot be threaded any further through the nut 102. At this point, a washer 104 and circlip 106 are fitted to the first end 51 of the plug 50 so that the nut 102 cannot work itself loose. The circlip 106 locates in the groove 59 provided at the first end 51 of the plug 50. The O-ring seal 57 located in the cylindrical portion 53 of the plug 50 ensures a sealing fit between the plug 50 and the bore 17.

Figure 5:
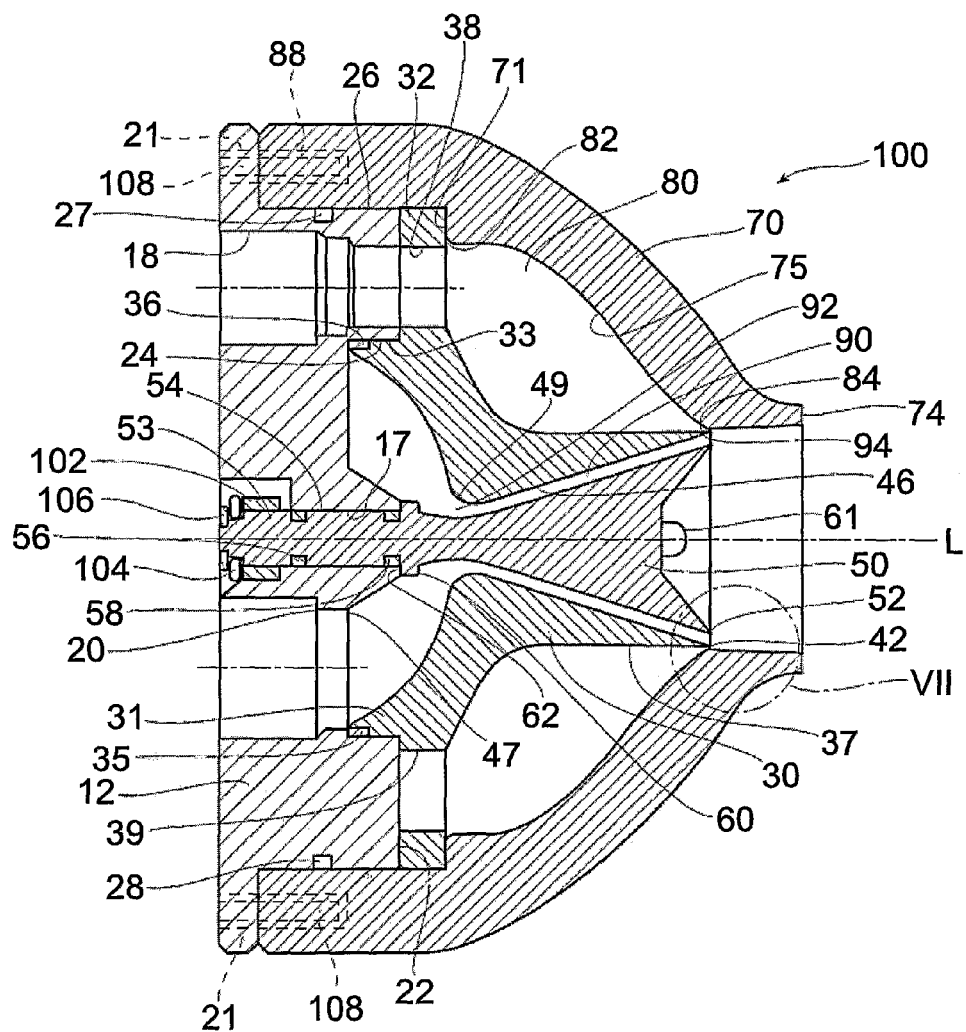
FIG. 5 shows a longitudinal section view through a mist-generating apparatus formed when the components of FIGS. 1-4 are assembled.

As can be seen in FIG. 5, once the plug 50 is axially and concentrically located in the bore 17, the conical portion 55 of the plug 50 lies between the throat portion 49 and outlet 48 of the bore 46 in the funnel 30. Consequently, the inner surface of the bore 46 and outer surface of the plug 50 now define a second fluid passage 90. The inlet 47 of the funnel bore 46 acts as the inlet of the second fluid passage 90, with the second fluid passage having a throat portion 92 adjacent the throat 49 of the bore 46, and an outlet 94 adjacent the respective second ends 42,52 of the funnel 30 and plug 50. As a result of the previously mentioned variations in the diameter of the bore 46 and the outward taper of the conical portion 55 of the plug 50, the second fluid passage 90 has a convergent-divergent internal geometry. In other words, the cross-sectional area of the throat portion 92 of the passage 90 is considerably smaller than that of the inlet 47 and the outlet 94. The cross sectional area of the passage 90 at the outlet 94 is greater than that at the throat portion 92, but less than that at the inlet 47. The total volume of the second fluid passage 90 from inlet 47 to outlet 94 may be between 24300 mm$^3$ and 25500 mm$^3$.

Once the plug 50 has been fixed to the base 12, the inspection port 39 can be used to measure the axial distance between the top surface of the annular projection 22 and the remote second ends 42, 52 of the funnel 30 and plug 50. This ensures that the base 12, funnel 30 and plug 50 are all correctly positioned relative to one another. At the same time, measuring instruments can be used to check the gap between the funnel 30 and plug 50 which forms the second fluid passage 90.

Once the measurement and positioning checks have been completed, the temporary locking ring can be removed and replaced with the cover 70. The cover 70 is axially placed on the base 12 such that the abutment 71 contacts the flange portion 32 of the funnel 30, and the cover is then concentric with the other components and the axis L. This sandwiches the flange portion 32 between the base 12 and cover 70, holding the base 12 and funnel 30 against one another. At the same time, the O-ring seal 28 ensures a sealing fit between the base 12 and cover 70. The cover 70 is aligned with the base 12 so that the threaded apertures 88 align with the apertures 21 in the base 12. A plurality of fixing screws 108 are then tightened into the threaded apertures 88 via the apertures 21 in the base 12. Once the screws 108 are fully tightened the heads of the screws 108 are at least flush with the rear face 14. A number of blind mounting holes 110 with internal threads are also provided on the rear face 14 of the base 12 for attaching the apparatus to a suitable mounting skid or the like.

As best seen in FIG. 5, once the cover 70 is successfully fitted, the second inner surface 75 of the cover 70 and the outer surface 37 of the funnel 30 define a first fluid passage 80 having an inlet 82 and an outlet 84. The inlet 82 is in fluid communication with the first fluid inlet 18 and first fluid passage 38. Due to the contours of the second inner surface 75 and outer surface 37 the first fluid passage 80 has a divergent-convergent internal geometry. In other words, the cross sectional area of a portion of the first fluid passage 80 intermediate the inlet 82 and outlet 84 is greater than the cross sectional area at either the inlet 82 or outlet 84. The cross sectional area of the first fluid passage 80 progressively reduces following the intermediate portion. The total volume of the first fluid passage 80 from inlet 82 to outlet 84 may be between 119000 mm$^3$ and 121500 mm$^3$.

Figure 7:
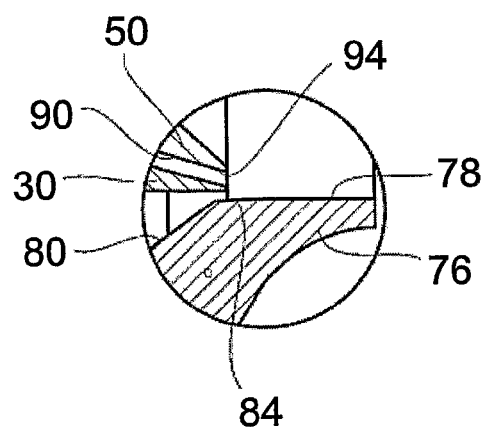
FIG. 7 is a detail view of the area marked "VII" in FIG. 5.

FIG. 7 shows a detail view of the respective outlets 84, 94 of the first and second fluid passages 80, 90. Once the various components are correctly assembled, the outlet 94 of the second fluid passage 90 is defined between the second ends 52, 42 of the plug 50 and funnel 30. The outlet 84 of the first fluid passage 80 is defined between the second end 42 of the funnel 30 and the inner surface 78 of the lip 76.

Figure 12:
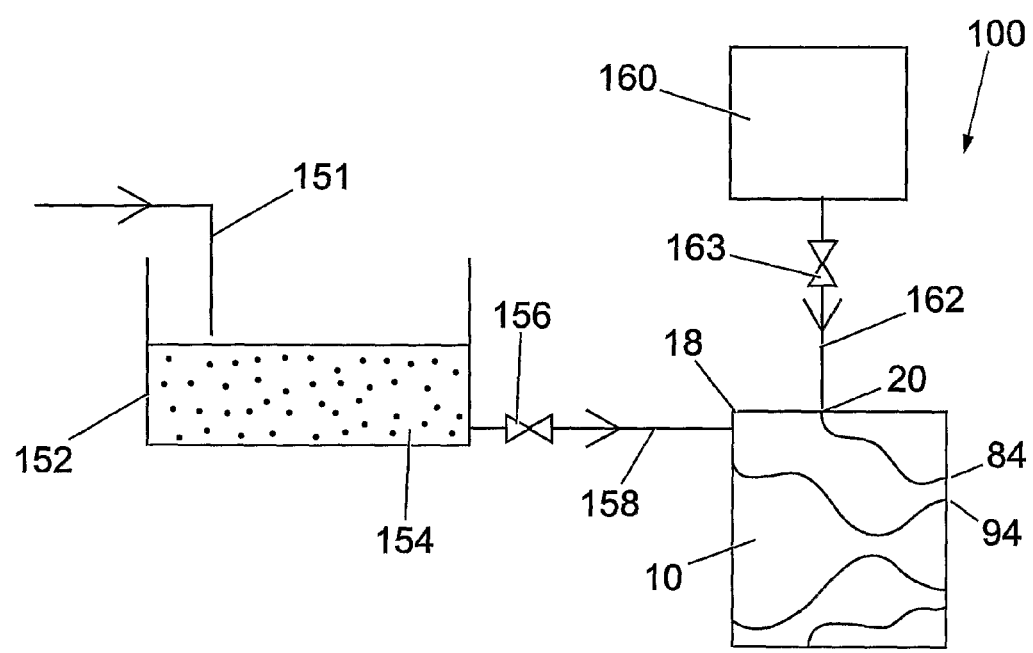
FIG. 12 is a schematic view of a decontaminating system.

FIG. 12 is a schematic representation of a decontaminating system 100, which includes a mist generating apparatus 10 of the type shown in FIGS. 1 to 5.

The system 100 comprises a decontaminant fluid reservoir 152 which has an outlet 154 controlled by an outlet valve 156.

The decontaminant fluid reservoir 152 may receive decontaminant fluid from a remote location via a supply line 151. Downstream of the decontaminant fluid reservoir 152 is the mist generating apparatus 10. The outlet of the decontaminant fluid reservoir 152 is fluidly connected to the first fluid inlet passage 18 of the mist generating apparatus 10 shown in FIG. 5 via a first processing line 158. Although not illustrated, the system 100 may also include one or more decontaminant preparation means for preparing the decontaminant fluid, e.g. the decontaminant preparation means may include a mixer system for mixing decontaminant in, for example, the form of a powder, into a solution.

If necessary, a pump or a compressor drawing air from the atmosphere may be provided on the first processing line 158 to pump or transfer the decontaminant fluid from the decontaminant fluid reservoir 152 to the mist generating apparatus 10. The valve 156 in the system 100, as well as the pump, or compressor, if present, may be controlled by a programmable system controller (not shown). It should also be appreciated that the decontaminant fluid reservoir 152 may also be pressurised by a compressor, or the like, or held under pressure, such that the decontaminant fluid may be transferred to the mist generating apparatus 10 by controlling the operation of the valve 156.

Although not illustrated, the system 100 may further comprise pressure regulation means for regulating the pressure of the decontaminant fluid in the decontaminant fluid reservoir 152 and/or flow rate regulation means for regulating the flow rate of the decontaminant fluid between the decontaminant fluid reservoir 152 to the mist generating apparatus 10.

Also shown in FIG. 12 is a transport fluid supply 160 (an example of a transport fluid source), which is connected to the second fluid inlet passage 20 of the mist generating apparatus 10 via a transport fluid supply line 162. A supply valve 163 controls the flow of the transport fluid from the supply 160.

If necessary, a pump or a compressor drawing air from the atmosphere may be provided on the transport fluid supply line 162 to pump the transport fluid from the transport fluid supply 160 to the mist generating apparatus 10. The valve 163 in the system 100, as well as the pump, or compressor, if present, may be controlled by a programmable system controller (not shown). It should also be appreciated that the transport fluid supply 160 may also be pressurised by a compressor, or the like, or held under pressure, such that the transport fluid may be transferred to the mist generating apparatus 10 by controlling the operation of the valve 163.

Although not illustrated, the system 100 may further comprise pressure regulation means for regulating the pressure of the transport fluid in the transport fluid supply 160 and/or flow rate regulation means for regulating the flow rate of the transport fluid between the transport fluid supply 160 to the mist generating apparatus 10.

The system 100 may also further comprise a power supply (not illustrated), such that the system 100 can operate as a "stand-alone" system.

The system 100 may also include a frame (not illustrated) on which the various components of the system 100 can be mounted. The frame may also include ground engaging wheel means and vehicle engaging means, such as a tow bar, such that the frame may be towed by a vehicle. The ground engaging wheel means may be operable remotely, thus allowing a user to be positioned a "safe" distance from the system 100. The dimensions of the frame (and components) are such that the system 100 is portable. For example, the frame could be sized to match a conventional pallet, such that the system 100 could be transported by a fork lift truck, or the like.

Although not illustrated, the system 100 may comprise a plurality of mist generating apparatuses. The plurality of mist generating apparatuses may be connected in series and/or in parallel to form an array. Furthermore, the system may be configured such that the apparatuses are moveable so that the nozzles may be arranged and positioned to suit a particular decontamination requirement.

The system may further comprise remote operating means (not shown) such that the mist generating apparatus, or apparatuses, may be operated and controlled remotely. This would allow the system 100 to be operated, for example, by a user at a "safe" distance from the system 100.

The system may further comprise one or more sensors (not shown) for automatically operating the system 100. The sensors could be configured to turn the system 100 "on" when one or more predetermined operating conditions are detected, such as when the sensors detect a decontaminant in the atmosphere. The sensors could, for example, be configured to open both decontaminant fluid and transport fluid valves when a decontaminant is detected in the atmosphere.

The process carried out by the system 100 will now be described, with reference to FIGS. 8*a* and 8*b*. Initially, supplies of decontaminant fluid and transport fluid are connected to the respective first and second fluid inlets 18, 20. Examples of decontaminant fluid may be a bleach or a biocide. Such decontaminants may be used in the cleaning of hospitals, or dealing with bio threats. Alternatively, the contaminants could be chemicals, in which case the decontaminants would be chemical neutralising formulations.

The decontaminant fluid is preferably introduced at a mass flow rate of between 0.5 kg/min and 20 kg/min at the first fluid inlet 18. The transport fluid is preferably a gas such as compressed air, steam, nitrogen or helium, for example. The transport fluid is preferably introduced to the second fluid inlet 20 at a pressure of between 4 bar and 18 bar. The decontaminant fluid passes through the first fluid passage 80 which narrows considerably in the direction of its outlet 84. As a result of this narrow gap at the outlet 84, the first fluid ejects out of the outlet 84 as a thin annulus of first fluid, initially following a path represented in FIG. 8*a* by the dotted line 120. The initial path of the decontaminant fluid 120 is substantially parallel to the inner surface 78 of the lip 76.

Due to the reduction and subsequent increase in the cross sectional area of the second fluid passage 90 between its inlet 47, throat 92 and outlet 94 the transport fluid entering the inlet 47 is accelerated to sonic and preferably supersonic velocities as it exits the outlet 94.

The decontaminant fluid and the transport fluid may be provided to the apparatus 10 in a decontaminant fluid-to-transport fluid mass flow ratio ranging from about 1:1 to about 4:1.

The angle of the second fluid passage 90 is such that the accelerated transport fluid stream, whose initial trajectory is shown as dotted line 122 in FIG. 8*a*, exits the outlet 94 and interacts with the annulus of decontaminant fluid issuing from the outlet 84. The angle of incidence between the decontaminant fluid and transport fluid streams 120, 122 is shown in FIG. 8*a* as angle α.

FIG. 8*b* shows schematically how an equivalent angle of expansion for the second fluid passage can be calculated when the cross sectional areas of the throat and outlet, and the equivalent path distance between the throat and outlet are known. E1 is the radius of a circle having the same cross sectional area as the throat of the second fluid passage. E2 is the radius of a circle having the same cross sectional area as the outlet of the second fluid passage. The distance d is the equivalent path distance between the throat and the outlet. An angle β is calculated by drawing a line through the top of E2 and E1 which intersects a continuation of the equivalent distance line d. This angle β can either be measured from a scale drawing or else calculated from trigonometry using the radii E1, E2 and the distance d. The equivalent angle of expansion γ for the second fluid passage can then be calculated by multiplying the angle β by a factor of two, where γ=2β.

For optimum performance of the apparatus 10, it has been found that the cross sectional area of the throat portion 92 of the second fluid passage 90 should preferably be between 20 mm² and 35 mm². The cross sectional area at the outlet 94 of the second fluid passage may be between 1.1 and 28 times larger than that of the throat portion 92, such that the area ratio between the throat 92 and outlet 94 of the second fluid passage 90 may be between 10:11 and 1:28. The cross sectional area at the outlet 94 of the second fluid passage may most preferably be between 1.4 and 5.5 times larger than that of the throat portion 92, such that the area ratio between the throat 92 and outlet 94 of the second fluid passage 90 is therefore most preferably between 5:7 and 2:11. This increase in cross sectional area between the throat portion 92 and outlet 94 creates an equivalent included angle of expansion γ for the second fluid passage 90 of between 1 and 40 degrees, and an angle γ which is most preferably between 2 and 13 degrees. Furthermore, the cross sectional area of the second fluid passage outlet 94 may be between 0.3 and 12 times larger than the cross sectional area of the first fluid passage outlet 84, such that the area ratio between the first fluid outlet 84 and second fluid outlet 94 is therefore between 10:3 and 1:12. The cross sectional area of the second fluid passage outlet 94 is most preferably between 1 and 6 times larger than the cross sectional area of the first fluid passage outlet 84, such that the area ratio between the first fluid outlet 84 and second fluid outlet 94 is therefore most preferably between 1:1 and 1:6.

The stream of transport fluid 122 coming into contact with the stream of decontaminant fluid 120 causes shear stripping of droplets from the annulus of decontaminant fluid 120 due to Kelvin-Helmholtz and Raleigh-Taylor instabilities on the decontaminant fluid surface. These instabilities cause ligaments of the decontaminant fluid to break off from the annulus and form dispersed droplet flow regime, thus atomising the decontaminant fluid. A dispersed droplet flow regime is considered to be a dispersed phase of decontaminant droplets in a continuous phase of transport fluid. As the droplets are torn from the decontaminant fluid stream 120 they are accelerated by the transport fluid, causing further shear break-up.

The transport fluid creates a turbulent region 124 as it moves away from the apparatus 10 and may have sufficient energy to induce low velocity air currents capable of transporting the droplets of decontaminant fluid through the surrounding space, preferably in a homogenous manner. This turbulent region 124 is caused by rapid changes in the pressure and velocity of the transport fluid generating numerous unsteady vortices and a swirling of the transport fluid. The turbulent region 124 applies acceleration and deceleration forces on the droplets, leading to a further atomisation of the droplets being carried by the transport fluid. This atomisation mechanism can be controlled by, amongst other things, controlling the momentum flux ratio between the decontaminant fluid and transport fluid.

The momentum flux ratio M is defined by the equation $$M \equiv \frac{(\rho_s \times U_t^2)}{(\rho_f \times U_d^2)}$$

where ρ=Fluid density
U=Fluid velocity
t represents transport fluid
d represents decontaminant fluid Thus, the momentum flux ratio between the decontaminant fluid and transport fluid can be controlled by varying the density or velocity of the decontaminant fluid and/or transport fluid. The velocity can be varied by adjusting the feed pressure while the density can be varied by changing the temperature of the fluid.

As most clearly shown in FIG. 8a, the decontaminant fluid and transport fluid streams 120, 122 issuing from their respective outlets 84, 94 are angled relative to one another at an angle of incidence α. The angle of incidence α is the angle between the initial trajectories of the streams 120, 122, shown as dotted lines in FIG. 8a. These initial trajectories are dictated by the inner wall 43 of the first fluid passage 80 and the outer wall 45 of the second fluid passage 90 at their respective outlets 84, 94. Thus, to obtain an angle of incidence in a desired range, the angle between these passage walls 43, 45 at the first and second fluid outlets 84, 94 should be in the same range. In the embodiment illustrated, both the inner first passage wall 43 and outer second passage wall 45 are defined by the funnel 30, as best seen in FIG. 2. The angle of incidence α causes the transport fluid stream 122 to impinge on the annulus forming the decontaminant fluid stream 120. The angle of incidence α is less than 90 degrees, and preferably between 5 and 30 degrees. Most preferably, the angle of incidence α is between 10 and 20 degrees.

The inner surface 78 of the lip 76 ensures that larger droplets torn from the decontaminant fluid stream 120 that could be projected away from the longitudinal axis L of the apparatus by the transport fluid stream 122 are prevented from doing so. Furthermore, droplets held against the inner surface 78 of the lip 76 are more easily atomised as they are subject to both the force of the transport fluid and the friction forces from the inner surface 78.

Figure 11:
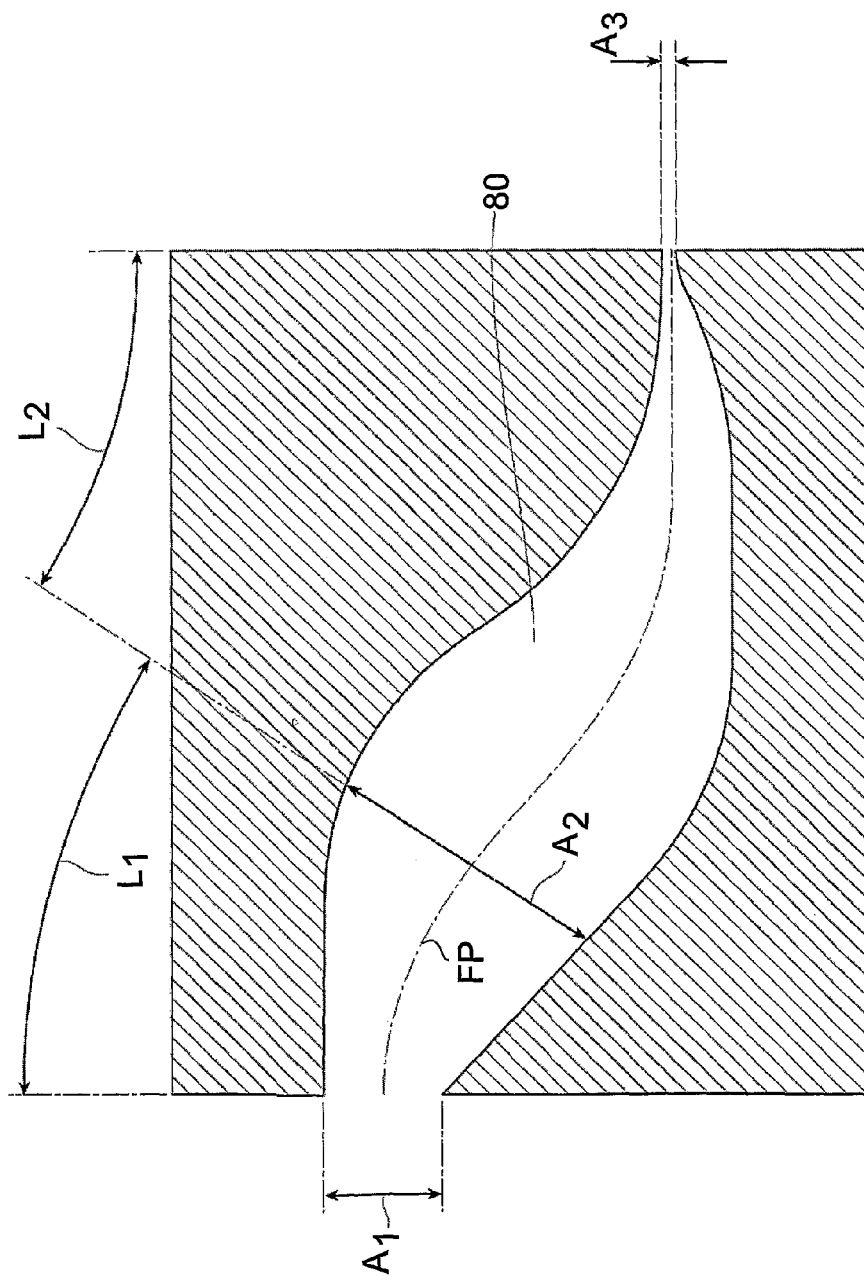
FIG. 11 is a cross-sectional view of a fluid passage in the mist-generating apparatus of FIG. 5.

The ability of the decontaminant fluid to form the desired thin annulus is a function of the first fluid passage 80. Shown in FIG. 11 is detailed cross-sectional view of the first fluid passage 80. The profile of the passage 80 can be defined by a curve that is a function of the three critical areas: (i) the inlet area A1 at the inlet area of the passage 80; (ii) the outlet area A3 at the outlet area of the passage 80; and (iii) the maximum intermediate area A3 between the inlet area A1 and the outlet area A3. Each of the critical areas A1, A2, A3 define an area coaxially disposed along the central fluid path FP of the passage 80. The areas A1, A2 and A3 are separated from one another along the path FP by a first fluid path distance L1 between areas A1 and A2 and a second fluid path distance L2 between areas A2 and A3.

Using the radii of the critical areas, A1, A2 and A3, the angular rate of change in radii from one area to the next adjacent can be determined by their trigonometric relationship. The radii increases from the inlet area A1 to the intermediate area A2. In the preferred embodiment, the ratio of the radii of the areas A1 to A2 can be about 1:1 to 1:50 is preferably about 1:1 to 1:5 and is more preferably about 1:1.5, so as to define an angular change between the radii from A1 to A2 of about 83° degrees (82.7°). The radii increases from the outlet area A3 to the intermediate area A2. In the preferred embodiment, the ratio of the radii of the areas A3 to A2 can be about 1:50 to 1:400 and is preferably about 1:100 to 1:300 and is more preferably about 1:278, so as to define an angular change between the radii from A3 to A1 of about 84° degrees (83.6°).

Figure 11A:
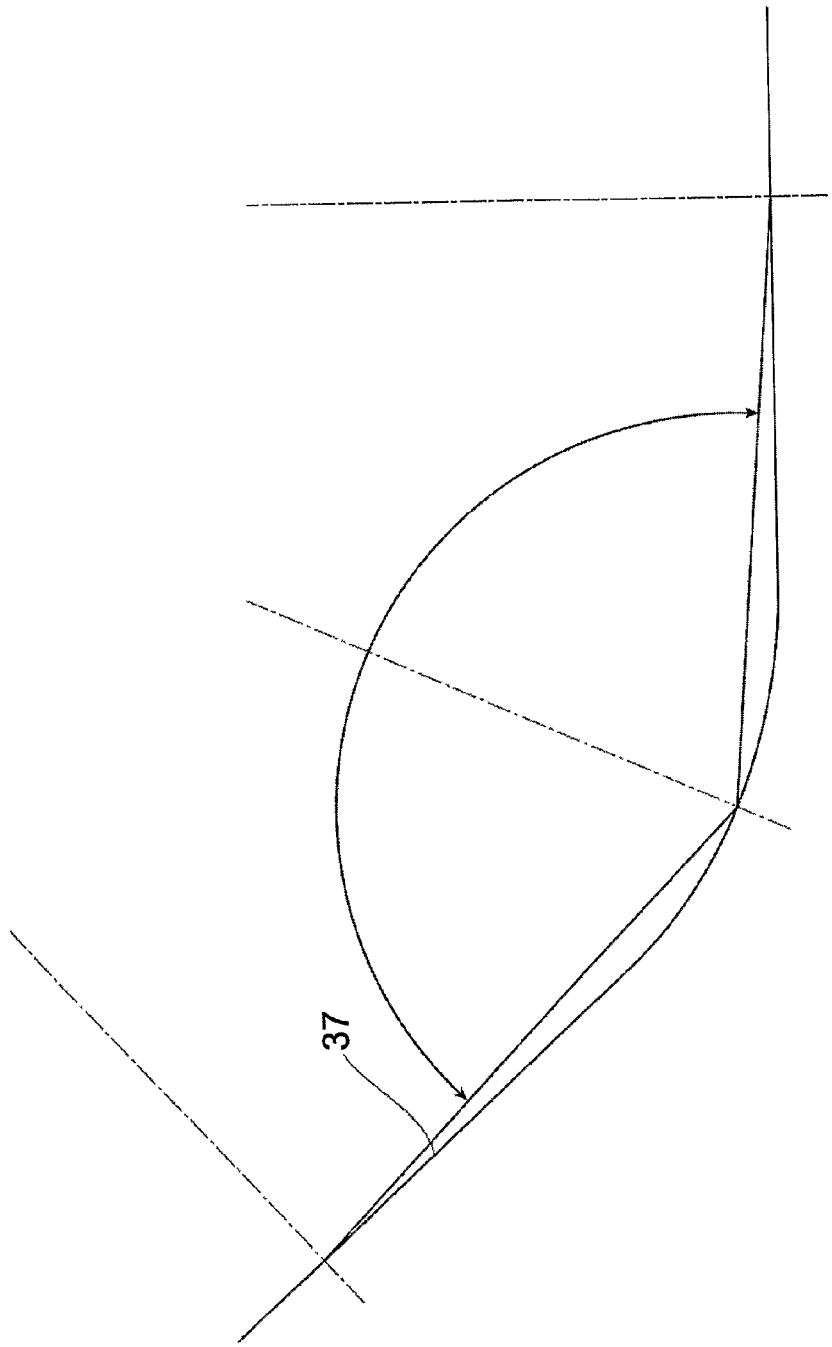
FIG. 11A is a detailed view of the fluid passage of FIG. 5.

The profile of the passage 80 is preferably smooth. Smoothness can be defined as the angular spacing between adjacent discrete segments which can approximate the surface profile. Referring to FIG. 11A, shown is a detailed view of the wall profile of the passage 80 has been broken up into discrete segments and the angle of change between each segment is measured. The discrete segments are each about 1 percent of the fluid path FP length. In a surface profile is smooth, then there is a small angular change from one segment to the next having a maximum change of about 90°, preferably a maximum of 45°, even more preferably a max of 45°, and is yet even more preferably less than 30 degrees. In contrast, if there is a sudden step in the profile, then the angular change is greater. In the preferred embodiment of the atomizer, the segmented profile of the passage 80 has a maximum angular change that is less than 30 degrees. More specifically, the surface of the passage 80 defined by the inner surface of the cover has a maximum angular change between adjacent segments of about 27° Degrees. The surface of the passage 80 defined by the outer surface of the funnel has a maximum angular change between adjacent segments of about 4.5° Degrees.

The system 100 is therefore capable of generating a decontaminating mist which is, for example, be suitable for decontaminating a person, object, area or volume.

The atomisation mechanism of the present invention is capable of atomising the decontaminant fluid into a mist in which a large proportion, preferably greater than 80%, more preferably 90%, of the decontaminant droplets, range in size from about 1 micron to about 10 microns and more preferably ranging from about 1 micron to about 5 microns.

Furthermore, under test conditions, the applicant supplied a decontaminant fluid at a flow rate of 13 liters per minute and the amount of decontaminant deposited on a "visible" surface (i.e. surface visible by direct line of sight from the apparatus) was 31.2 mg/cm². The amount of decontaminant deposited on a "non-visible" surface was 4 mg/cm². These figures are based on a fill time of 10 minutes and a dwell time of 3 minutes. For a decontaminant fluid flow rate of 0.5 liters per minute, the amount of decontaminant deposited on a "visible" surface (i.e. surface visible by direct line of sight from the apparatus) was 6.1 mg/cm². The amount of decontaminant deposited on a "non-visible" surface was 4.5 mg/cm². These figures are based on a fill time of 10 minutes and a dwell time of 20 minutes. The wording "non-visible" should be interpreted as meaning not within the line of sight from the fluid outlet of the apparatus.

The suspension time of the decontaminant mist generated by the system 100 may be up to 30 minutes or more, depending on ambient conditions.

The operation of the system 100 is adjustable and controllable, such that all the parameters and performance figures detailed above can be varied depending on the operational requirements of the system 100.

The decontaminant mist generated by the system 100 decontaminates by any of the following mechanisms (i) Nucleation Precipitation, where the decontaminant droplets and the contaminant particles stick together, thus increasing the mass which results in the contaminant dropping out of the atmosphere; (ii) Chemical Neutralisation, where a chemical reaction takes place between the decontaminant droplets and the contaminant particles, thus neutralising the contaminant; and (iii) Solution Precipitation, where the decontaminant droplets collide with the contaminant particles, thus creating a solution of increased mass, which results in the contaminant dropping out of the atmosphere. Due to the high density and high number of dispersed droplets and the turbulent nature of the decontaminant mist, the system is capable of maximising the number of collisions between decontaminant and contaminant.

FIGS. 9 and 10 show views of an alternative embodiment of a mist-generating apparatus 100'. The alternative embodiment of the apparatus, generally designated 100', shares a number of components with the previously described embodiment and atomises the first fluid in the same manner as described above. However, the alternative embodiment does also have a number of differences from the first embodiment. Most noticeably, the second end 74' of the cover 70' does not have a protruding lip. The second end 74' is therefore adjacent the first and second fluid outlets 84',94'. The funnel 30' of this alternative embodiment does not have a radially projecting flange portion which is sandwiched between the cover 70' and the base 12'. Instead, the funnel 30' is secured directly to the base 12' by a number of fixing screws (not shown). Additionally, instead of being secured together by screw fixings the cover 70' has an internal thread on its inner surface 73' which cooperates with an external thread on the outer surface 26' of the base 12'. The cover 70' can therefore be threaded onto the base 12', and turning the cover 70' relative to the base 12' will adjust the axial distance between the cover 70' and both the base 12' and the funnel 30' directly secured to the base 12'.

As seen best in FIG. 10, the first fluid outlet 84' has been adapted in several ways in the alternative embodiment. Firstly, the width of the gap between the second ends 42',74' of the funnel 30' and cover 70' which forms the first fluid outlet 84' has been increased. Increasing the gap widens the first fluid outlet 84' and reduces the exit velocity of the decontaminant fluid for the same flow rate condition. Secondly, as the axial distance between the cover 70' and the funnel 30' can be adjusted in this embodiment, the angle of projection and exit velocity of the decontaminant fluid can also be adjusted. Adjusting the axial position of the cover 70' relative to the base 12' and funnel 30' adjusts the relative axial positions of the second end 74' of the cover 70' and the second end 42' of the funnel 30', both of which define the first fluid outlet 84'. The adjustment of these components therefore also adjusts the gap size of the first fluid outlet 84' and initial path 120' of the decontaminant fluid stream as it exits through the first fluid outlet 84'. As a result, the more the cover 70' is screwed onto the base 12' the more the initial path of the decontaminant fluid stream 120' issuing from the outlet 84' will diverge from the longitudinal axis L' of the apparatus 100'. In the first embodiment, the angle of projection was substantially parallel with the longitudinal axis of the apparatus. The variation in the angle of projection also reduces the angle of incidence α' between the first and second fluid streams 120',122' issuing from their respective outlets 84',94'.

The plug 50' in the alternative embodiment has a longer threaded surface 54' and no lip portion limiting its axial position relative to the base 12'. The bore 17' in the base 12' has an internal thread which engages the threaded surface 54' of the plug 50'. As a result, the axial position of the plug 50' relative to the base 12' and the other main components can be adjusted depending upon the amount that the plug 50' is screwed into the base 12'. This also allows the width of the second fluid passage 90' and outlet 94' to be adjusted, as the position of the plug 50' can be adjusted relative to the funnel 30'. Consequently, the adjustment of the plug 50' also adjusts the area ratio between the throat and outlet of the second fluid passage, as well as the equivalent angle of expansion of the second fluid passage. Once the plug 50' has been positioned such that the area ratio between the first and second outlets and the equivalent angle of expansion γ are within the ranges set forth above, a lock nut 102' is fitted over the first end 51' of the plug 50' protruding from the rear face 14' of the base 12'.

The mist generating apparatus has a single supply channel for each of the decontaminant and transport fluids. The supply channels are substantially parallel with the longitudinal axis of the apparatus, thereby reducing the supply pressures needed to supply the fluids. Having single supply channels for each fluid which are substantially parallel to the longitudinal axis of the apparatus allows the apparatus and supply lines to be more easily manufactured, assembled and installed on a mounting skid or the like, in comparison to mist generators which have one or more supply channels which enter the apparatus perpendicular to the longitudinal axis.

The geometry of the fluid passages and their respective outlets also provides the present invention with improved performance compared with existing mist generators in terms of efficiency (the amount of transport fluid used to atomise the decontaminant fluid) and the degree of atomisation of the decontaminant fluid. Specifically, the area ratio between the first and second fluid outlets, and the angle of incidence between the two streams of the fluid exiting the outlets improve atomisation performance in the present invention. By providing an area ratio between the respective outlets as detailed above, the present invention provides a thin film sheet of decontaminant fluid which can be atomised more efficiently by the transport fluid. The smaller exit area of the first fluid outlet also increases the exit velocity of the decontaminant fluid, which in itself can lead to a degree of atomisation of the decontaminant fluid as it exits the apparatus. Providing an angle of incidence between the two streams which falls within the ranges detailed above provides improved atomisation of the decontaminant fluid (in terms of droplet size and droplet distribution) whilst reducing the risk of the atomised decontaminant fluid droplets coalescing together again. The greater the angle of incidence between the streams, the greater the initial momentum transfer from the transport fluid to the decontaminant fluid. However, a large angle of incidence also can lead to the decontaminant fluid film sheet converging when it comes into contact with the transport fluid stream, increasing the risk that some of the atomised decontaminant fluid droplets will coalesce back together.

Using the transport fluid stream to create a turbulent region outside the apparatus ensures further atomisation of the decontaminant fluid, again improving the atomisation performance of the present invention. Thus, the present invention provides process and system for generating a decontaminating mist which (i) generates a mist with the desired decontaminant droplet size, and (ii) generates turbulence in the protection space for substantially homogenous distribution of the decontaminant droplets throughout the volume of the surrounding space.

Due to size of decontaminant particle produced in the mist and the method of producing the mist, the present invention is capable of defeating airborne contaminants and surface contaminants. The method of generating the mist (particularly the turbulence created) means that the decontaminating mist is capable of impinging upon complex surfaces, including "non-visible" surfaces. Since the system is capable of covering far greater surface areas than conventional systems, the present invention reduces the amount of decontaminant chemical which has to be used in the system. This reduction can be up to 80% over conventional systems. This reduces the cost involved in the decontamination process. Furthermore, as the decontaminant is created in the form of a mist instead of a liquid, there is less "water damage" caused to equipment in the decontamination area, such as computers, or the like.

Also, since the decontaminant is in the form of a mist, there are no large amounts of fluid etc. to clean after decontamination process. Also the system and method of the invention provide a more efficient decontamination process, as the decontaminant mist is generated in a quick and thorough manner, which means that the decontamination takes less time than conventional methods. As an example, for a room with a volume of approximately 280 m$^3$ the system, operating with a decontaminant fluid-to-transport fluid mass flow ratio of 3:1, will make the room visually dense in approximately 60 to 90 seconds.

The method in which the apparatus is assembled also has benefits. The base, funnel, plug and cover are all assembled concentrically in such a way that the gaps defining the fluid passages and outlets between the components are consistent along the length and around the circumference of the apparatus. Furthermore, as each of the funnel, plug and cover are attached or mounted to the base plate, the components have a common reference point. This ensures that tolerance errors are minimised instead of being multiplied, as is often the case in prior art assemblies where the components are assembled together without a common reference.

The cover member having the axially projecting lip prevents damage to the funnel and plug if the apparatus is dropped. The relative positions of these components, and hence the geometry of the first and second passages, is therefore protected. Additionally, the inner surface of the lip ensures that the apparatus has directionality, i.e. the atomised droplets can be directed towards a chosen location. Furthermore, droplets held against the inner surface of the lip are more easily atomised as they are subject to both the force of the transport fluid and the friction forces from the inner surface. However, it should be understood that this embodiment may alternatively have a lip which projects a relatively short distance, e.g. a few millimeters, or the lip may be omitted from the embodiment. In these instances, the atomising process described above will take place substantially outside of the mist-generating apparatus.

In the embodiment where the cover member has no projecting lip, there is no radial constriction of the fluid streams. Therefore the streams are allowed to expand radially away from the longitudinal axis L of the apparatus at an earlier stage than they would if there was a lip present. This creates a greater degree of turbulence in the transport fluid, which can enhance the atomisation of the decontaminant fluid. Additionally, the resulting mist plume has a wider spread, which can be beneficial in a situation where the apparatus is to fill a particular volume with the mist as opposed to directing the plume towards a specific location.

One or more of the fixing screws used in the assembly of the apparatus may be replaced with an alternative mechanical fixture where appropriate. Suitable examples include fixing bolts, clamps, or a combination thereof. One or more of the mechanical fixtures may be a tamper proof or tamper evident fixture in order to either prevent or highlight disassembly of the apparatus following installation.

Instead of using a threaded arrangement as in the alternative embodiment, the adjustment of the axial position of the cover relative to the base may alternatively be achieved by inserting shims between the two components and then tightening the two components together using mechanical fixtures in the same manner as that of the first embodiment.

Whilst it is preferred that the apparatus is formed in the manner described from a base, funnel, plug and cover member, it should be recognised that the apparatus is not limited to the formation of the various fluid channels and passages using these specific components. The desired fluid channels and passages may be created within the apparatus in an alternative manner to that described. For example, the channels and passages may be formed by drilling the apparatus, or else by casting the apparatus with the channels and passages formed therein.

Although the apparatus is preferably manufactured from stainless steel, alternative materials sharing the same properties may also be used instead. The primary requirements of the material are resistance to corrosion, chemicals and wear. It is also preferable that the material is easily machined or formed, and relatively inexpensive. Possible alternative materials include metals such as aluminium and brass, and metal alloys such as tungsten. Plastics or ceramic materials having the aforementioned properties may also be used.

While the transport fluid is preferably a gas, it is not to be considered as limited to the examples of gas given in the foregoing disclosure. Other compressible fluids having similar properties to the gases disclosed may also be used without affecting the manner of operation of the present invention. The transport fluid should preferably be easily obtainable, relatively inexpensive and non-corrosive. It may also be beneficial to use a transport fluid which has the additional benefits of being generated on site (e.g. via a compressor).

Although the system has been described above as being portable, it should be appreciated that the system could be fixed permanently to a structure, outdoor area, building or the like. The system could, for example, be built into a building during construction in a similar manner to a fire sprinkler system. The system could also be retro-fitted to any existing structures, areas, buildings etc. or formed as a separate decontamination room or enclosure. Furthermore, the system could also be incorporated into a transportable temporary installation, such as a tent etc. For example, the system could be incorporated into a tent, or the like, for decontaminating vehicles.

Although the first fluid passage is illustrated and described above as having an intermediate portion located between the first fluid inlet and the first fluid outlet which has a cross sectional area which is larger than that of either the first fluid inlet or the first fluid outlet, it should be appreciated that the first fluid passage may have a cross sectional area which converges between the first fluid inlet and the first fluid outlet.

It should also be appreciated that the term atomised does not necessarily mean that the decontaminant fluid is fully atomised, it should be appreciated that the decontaminant fluid may be at least partially atomised, i.e. where the decontaminant fluid is not fully atomised.

These and other modifications and improvements may be incorporated without departing from the scope of the invention.

What is claimed is:

1. A decontamination system comprising:

a decontaminant reservoir;

a transport fluid source; and a mist generating apparatus having a longitudinal axis, the apparatus comprising:

a curved divergent-convergent first fluid passage having a first fluid inlet in fluid communication with the decontaminant reservoir, the first fluid inlet defining an inlet area, an annular first fluid outlet defining an outlet area, and an intermediate portion defining an intermediate area greater than each of the inlet area and the outlet area, the curved divergent-convergent first fluid passage having an outer surface with a curved profile between at least the intermediate area and outlet area; and a convergent-divergent second fluid passage having a second fluid inlet in fluid communication with the transport fluid source and an annular second fluid outlet, wherein the first fluid passage surrounds the second fluid passage, and the first and second outlets are oriented relative to one another such that they have an angle of incidence between 5 and 30 degrees; wherein a cross-sectional area of the second fluid outlet is larger than a cross-sectional area of the first fluid outlet; and the second fluid passage includes a throat portion located between the second fluid inlet and the second fluid outlet, the throat portion having a smaller cross sectional area than that of either the second fluid inlet or second fluid outlet.

2. The system of claim 1, wherein the area ratio between the throat portion and the second fluid outlet is between 2:3 and 1:4.

3. The system of claim 1, wherein the first and second passages are coaxial with the longitudinal axis of the apparatus.

4. The system of claim 1, wherein the mist generating apparatus further comprises a first fluid supply channel having a first end adapted to be connected to the decontaminant reservoir and a second end connected to the first fluid inlet, and a second fluid supply channel having a first end adapted to be connected to the transport fluid source and a second end connected to the second fluid inlet, wherein the first and second supply channels are substantially parallel to the longitudinal axis of the apparatus.

5. The system of claim 4, wherein the mist generating apparatus comprises a base member that contains the first and second supply channels.

6. The system of claim 5, wherein the mist generating apparatus further comprises a funnel member and an elongate plug member, wherein the funnel member has a bore and is adapted to coaxially locate upon the base such that the bore communicates with the second fluid supply channel, and wherein the plug member is adapted to be attached to the base member such that a portion of the plug lies within the bore and the second fluid passage is defined between the funnel and the plug.

7. The system of claim 6, wherein the mist generating apparatus further comprises a cover member which encloses the base member, the funnel member and the plug member such that the first fluid passage is defined between an outer surface of the funnel and an inner surface of the cover member.

8. The system of claim 7, wherein the cover member has a first end adapted to coaxially locate upon the base member and be attached thereto, and a second end having an outlet adapted to communicate with the first and second fluid outlets.

9. The system of claim 8, wherein the second end of the cover includes an axially projecting lip portion, the lip portion defining an aperture in communication with the first and second fluid outlets.

10. The system of claim 7, wherein the plug member has a first end which attaches to the base member and a second end which defines the second fluid passage, wherein the second end is concave.

11. The system of claim 7, wherein the funnel member includes a radially projecting flange portion, wherein the flange portion is sandwiched between the base member and the cover member to maintain the axial position of the funnel member relative to the base member.

12. The system of claim 7, wherein the axial position of the cover member may be adjusted relative to the base member.

13. The system of claim 6, wherein the plug member is threaded onto the base such that the axial position of the plug member may be adjusted relative to the base and the funnel member.

14. A system for decontaminating an enclosed space, wherein the system includes the system of claim 1.

15. A decontamination room or enclosure including a decontaminating system as claimed in claim 1.

16. A decontaminating system comprising:

a decontaminant reservoir;

a transport fluid source; and a mist generating apparatus having a longitudinal axis, the apparatus comprising:

a curved divergent-convergent first fluid passage having a first fluid inlet in fluid communication with the decontaminant reservoir, the first fluid inlet defining an inlet area, an annular first fluid outlet defining an outlet area, and an intermediate portion defining an intermediate area greater than each of the inlet area and the outlet area, the curved divergent-convergent first fluid passage having an outer surface with a curved profile between at least the intermediate area and outlet area; and a convergent-divergent second fluid passage having a second fluid inlet in fluid communication with the transport fluid source and an annular second fluid outlet, wherein the first fluid passage surrounds the second fluid passage, and the first and second fluid outlets are oriented relative to one another such that they have an angle of incidence of less than 90 degrees; wherein a cross-sectional area of the second fluid outlet is larger than a cross-sectional area of the first fluid outlet; and the second fluid passage includes a throat portion located between the second fluid inlet and the second fluid outlet, the throat portion having a smaller cross sectional area than that of either the second fluid inlet or the second fluid outlet such that the area ratio between the throat portion and the second fluid outlet is between 2:3 and 1:4.

17. The system of claim 16, wherein the first and second passages are coaxial with the longitudinal axis of the apparatus.

18. The system of claim 16, wherein the mist generating apparatus further comprises a first fluid supply channel having a first end adapted to be connected to the decontaminant reservoir and a second end connected to the first fluid inlet, and a second fluid supply channel having a first end adapted to be connected to the transport fluid source and a second end connected to the second fluid inlet, wherein the first and second supply channels are substantially parallel to the longitudinal axis of the apparatus.

19. The system of claim 18, wherein the mist generating apparatus comprises a base member that contains the first and second supply channels.

20. The system of claim 19, wherein the mist generating apparatus further comprises a funnel member and an elongate plug member, wherein the funnel member has a bore and is adapted to coaxially locate upon the base such that the bore communicates with the second fluid supply channel, and wherein the plug member is adapted to be attached to the base member such that a portion of the plug lies within the bore and the second fluid passage is defined between the funnel and the plug.

21. The system of claim 20, wherein the mist generating apparatus further comprises a cover member which encloses the base member, the funnel member and the plug member such that the first fluid passage is defined between an outer surface of the funnel and an inner surface of the cover member.

22. The system of claim 21, wherein the cover member has a first end adapted to coaxially locate upon the base member and be attached thereto, and a second end having an outlet adapted to communicate with the first and second fluid outlets.

23. The system of claim 22, wherein the second end of the cover includes an axially projecting lip portion, the lip portion defining an aperture in communication with the first and second fluid outlets.

24. The system of claim 20, wherein the plug member has a first end which attaches to the base member and a second end which defines the second fluid passage, wherein the second end is concave.

25. The system of claim 21, wherein the funnel member includes a radially projecting flange portion, wherein the flange portion is sandwiched between the base member and the cover member to maintain the axial position of the funnel member relative to the base member.

26. The system of claim 21, wherein the axial position of the cover member may be adjusted relative to the base member.

27. The system of claim 20, wherein the plug member is threaded onto the base such that the axial position of the plug member may be adjusted relative to the base and the funnel member.

28. A method of generating a decontaminating mist, the method comprising:
   passing a decontaminant fluid through a curved divergent convergent first fluid passage of a mist generating apparatus, wherein the first fluid passage has an annular first fluid outlet defining an outlet area, and an intermediate portion defining an intermediate area greater than each of an inlet area and the outlet area, the curved divergent-convergent first fluid passage having an outer surface with a curved profile between at least the intermediate area and outlet area;
   passing a transport fluid through a convergent-divergent second fluid passage of the mist generating apparatus, wherein the second fluid passage has an annular second fluid outlet and a throat portion, the throat portion having a smaller cross sectional area than the second fluid outlet, wherein the first and second outlets are oriented relative to one another such that they have an angle of incidence between 5 and 30 degrees; wherein a cross-sectional area of the second fluid outlet is larger than a cross-sectional area of the first fluid outlet;
   accelerating the flow of transport fluid through the throat portion of the second fluid passage; and
   ejecting the decontaminant and transport fluids from their respective outlets such that a stream of accelerated transport fluid issuing from the second fluid outlet imparts a shear force on a stream of decontaminant fluid issuing from the first fluid outlet, thereby at least partially atomising the decontaminant fluid to create a dispersed droplet flow regime.

29. A method of generating a decontaminating mist, the method comprising:
   passing a decontaminant fluid through a curved divergent-convergent first fluid passage of a mist generating apparatus, wherein the first fluid passage has an annular first fluid outlet defining an outlet area, and an intermediate portion defining an intermediate area greater than each of an inlet area and the outlet area, the curved divergent-convergent first fluid passage having an outer surface with a curved profile between at least the intermediate area and outlet area;
   passing a transport fluid through a convergent-divergent second fluid passage of the mist generating apparatus, wherein the convergent-divergent second fluid passage has an annular second fluid outlet and a throat portion, the throat portion having a smaller cross sectional area than the second fluid outlet such that the area ratio between the throat portion and the second fluid outlet is between 2:3 and 1:4, wherein the first and second fluid outlets are oriented relative to one another such that they have an angle of incidence of less than 90 degrees; wherein a cross-sectional area of the second fluid outlet is larger than a cross-sectional area of the first fluid outlet;
   accelerating the flow of transport fluid through the throat portion of the second fluid passage; and
   ejecting the decontaminant and transport fluids from their respective outlets such that a stream of accelerated transport fluid issuing from the second fluid outlet imparts a shear force on a stream of decontaminant fluid issuing from the first fluid outlet, thereby at least partially atomising the decontaminant fluid to create a dispersed droplet flow regime.

30. The method of claim 28, wherein the method comprises the further step of creating a turbulent region in the transport fluid downstream of the outlets; and passing the dispersed droplet flow regime through the turbulent region, thereby further atomising the dispersed droplet flow regime.

31. The method of claim 28, wherein the method comprises the further step of controlling the momentum flux ratio between the decontaminant fluid and the transport fluid by varying the velocity and/or density of the decontaminant fluid and the transport fluid.

32. The method of claim 28, wherein the method comprises the further step of adjusting the cross sectional area of the first fluid outlet in order to vary the exit velocity of the decontaminant fluid stream.

33. The method of claim 32, wherein the exit velocity is supersonic.

34. A method for decontaminating an enclosed space by generating a decontaminating mist according to the method of claim 28.

35. A method of providing a decontamination system comprising:
   providing a decontaminant reservoir;
   providing a transport fluid source; and
   providing a mist generating apparatus having a longitudinal axis, the apparatus comprising:
   a curved divergent-convergent first fluid passage having a first fluid inlet in fluid communication with the decontaminant reservoir, the first fluid inlet defining an inlet area, an annular first fluid outlet defining an outlet area, and an intermediate portion defining an intermediate area greater than each of the inlet area and the outlet area, the curved divergent-convergent first fluid passage having an outer surface with a curved profile between at least the intermediate area and outlet area; and
   a convergent-divergent second fluid passage having a second fluid inlet in fluid communication with the transport fluid source and an annular second fluid outlet,
   wherein the first fluid passage surrounds the second fluid passage, and the first and second outlets are oriented relative to one another such that they have an angle of incidence between 5 and 30 degrees; wherein a cross-sectional area of the second fluid outlet is larger than a cross-sectional area of the first fluid outlet; and the second fluid passage includes a throat portion located between the second fluid inlet and the second fluid outlet, the throat portion having a smaller cross sectional area than that of either the second fluid inlet or second fluid outlet.

36. A method of providing a decontaminating system comprising:

providing a decontaminant reservoir;

providing a transport fluid source; and providing a mist generating apparatus having a longitudinal axis, the apparatus comprising:

a curved divergent-convergent first fluid passage having a first fluid inlet in fluid communication with the decontaminant reservoir, the first fluid inlet defining an inlet area, an annular first fluid outlet defining an outlet area, and an intermediate portion defining an intermediate area greater than each of the inlet area and the outlet area, the curved divergent-convergent first fluid passage having an outer surface with a curved profile between at least the intermediate area and outlet area; and a convergent-divergent second fluid passage having a second fluid inlet in fluid communication with the transport fluid source and an annular second fluid outlet, wherein the first fluid passage surrounds the second fluid passage, and the first and second outlets are oriented relative to one another such that they have an angle of incidence of less than 90 degrees; wherein a cross-sectional area of the second fluid outlet is larger than a cross-sectional area of the first fluid outlet; and the second fluid passage includes a throat portion located between the second fluid inlet and the second fluid outlet, the throat portion having a smaller cross sectional area than that of either the second fluid inlet or the second fluid outlet such that the area ratio between the throat portion and the second fluid outlet is between 2:3 and 1:4.

* * * * *